(12) United States Patent
Heisler

(10) Patent No.: US 8,313,502 B2
(45) Date of Patent: Nov. 20, 2012

(54) ENDOSCOPIC CUTTING INSTRUMENTS HAVING IMPROVED CUTTING EFFICIENCY AND REDUCED MANUFACTURING COSTS

(75) Inventor: Gary R. Heisler, St. Pete Beach, FL (US)

(73) Assignee: Target Medical Innovations, LLC, St. Pete Beach, FL (US)

( * ) Notice: Subject to any disclaimer, the term of this patent is extended or adjusted under 35 U.S.C. 154(b) by 0 days.

(21) Appl. No.: 13/301,156

(22) Filed: Nov. 21, 2011

(65) Prior Publication Data

US 2012/0065658 A1    Mar. 15, 2012

Related U.S. Application Data

(60) Division of application No. 12/175,428, filed on Jul. 17, 2008, now Pat. No. 8,177,803, which is a continuation-in-part of application No. 11/634,102, filed on Dec. 6, 2006, now Pat. No. 7,666,200.

(60) Provisional application No. 60/964,590, filed on Aug. 13, 2007, provisional application No. 61/011,828, filed on Jan. 22, 2008, provisional application No. 60/831,986, filed on Jul. 19, 2006.

(51) Int. Cl.
 *A61B 17/32* (2006.01)
(52) U.S. Cl. ...................................................... 606/171
(58) Field of Classification Search .......... 606/167–171, 606/180, 106, 107, 79, 80, 84
See application file for complete search history.

(56) References Cited

U.S. PATENT DOCUMENTS

| | | | |
|---|---|---|---|
| 5,217,479 A | 6/1993 | Shuler | 606/180 |
| 5,226,910 A | 7/1993 | Kajiyama et al. | 606/171 |
| 5,269,798 A * | 12/1993 | Winkler | 606/170 |
| 5,693,063 A | 12/1997 | Van Wyk et al. | 606/167 |
| 5,709,698 A * | 1/1998 | Adams et al. | 606/180 |
| 5,766,199 A * | 6/1998 | Heisler et al. | 606/180 |
| 5,843,106 A | 12/1998 | Heisler | 606/167 |
| 6,053,928 A | 4/2000 | Van Wyk et al. | 606/167 |
| 6,419,684 B1 | 7/2002 | Heisler et al. | 606/170 |
| 6,447,525 B2 | 9/2002 | Follmer et al. | 606/159 |
| 2003/0083684 A1 | 5/2003 | Cesarini et al. | 606/170 |
| 2005/0065538 A1 | 3/2005 | Van Wyk | 606/159 |
| 2006/0217751 A1 | 9/2006 | O'Quinn et al. | 606/180 |

* cited by examiner

*Primary Examiner* — Elizabeth Houston
(74) *Attorney, Agent, or Firm* — Chalin A. Smith; Smith Patent Consulting

(57) ABSTRACT

The present invention is directed to improving the cutting efficiency and reducing the manufacturing costs associated with endoscopic cutting instruments by eliminating the distal bearing surfaces or providing means for making the contact at the distal bearing intermittent so that surfaces do no undergo high localized heat and galling. In one embodiment, this goal is achieved by modifying or removing the axial constraints on the inner sliding member that are characteristic of conventional endoscopic shavers. In another embodiment, the improved cutting efficiency and reduced manufacturing cost is achieved by eliminating a closed end characteristic of conventional endoscopic shavers (e.g., removing the closed end of either the inner sliding member or the outer sliding member to thereby eliminate the associated bearing surface formed therebetween).

17 Claims, 16 Drawing Sheets

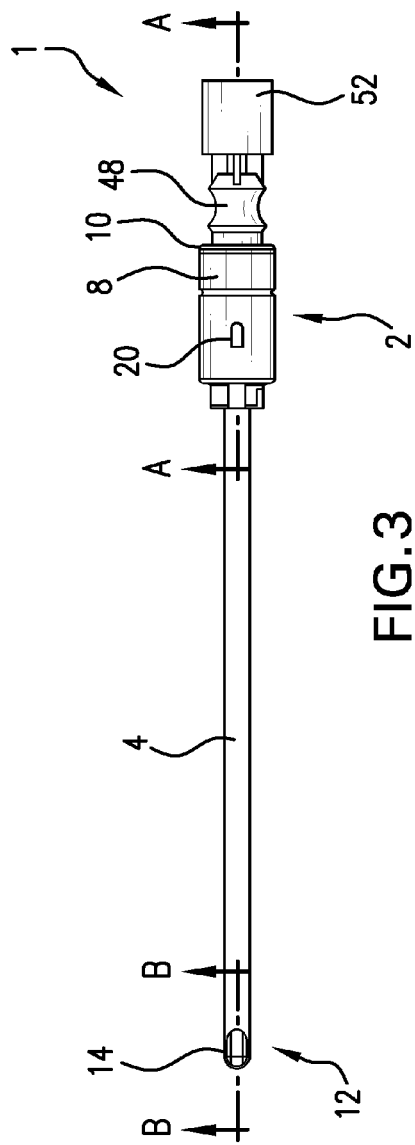
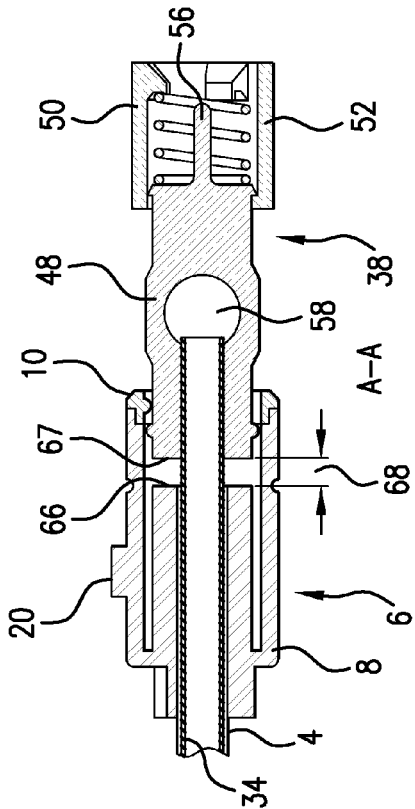
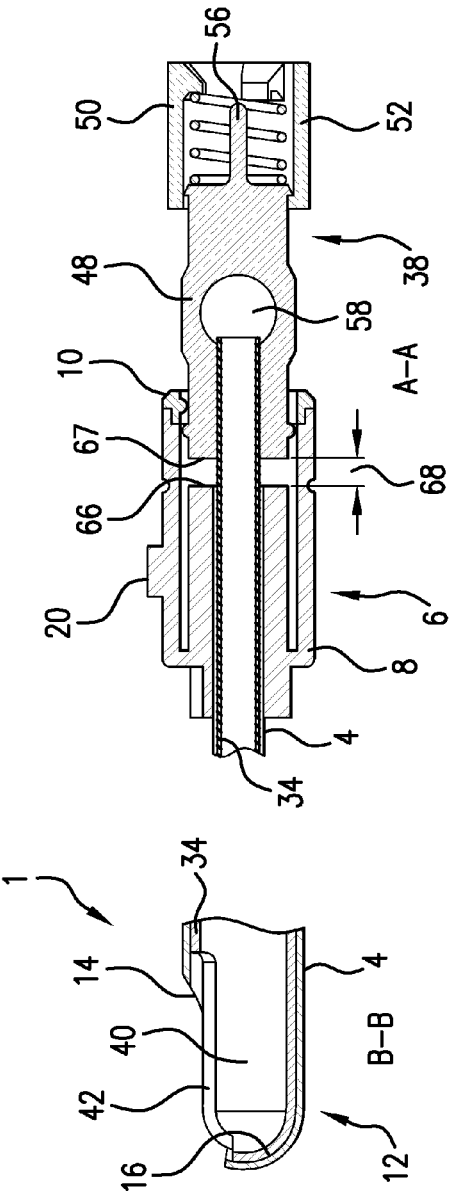
FIG. 3
PRIOR ART
FIG. 4
PRIOR ART
FIG. 5
PRIOR ART

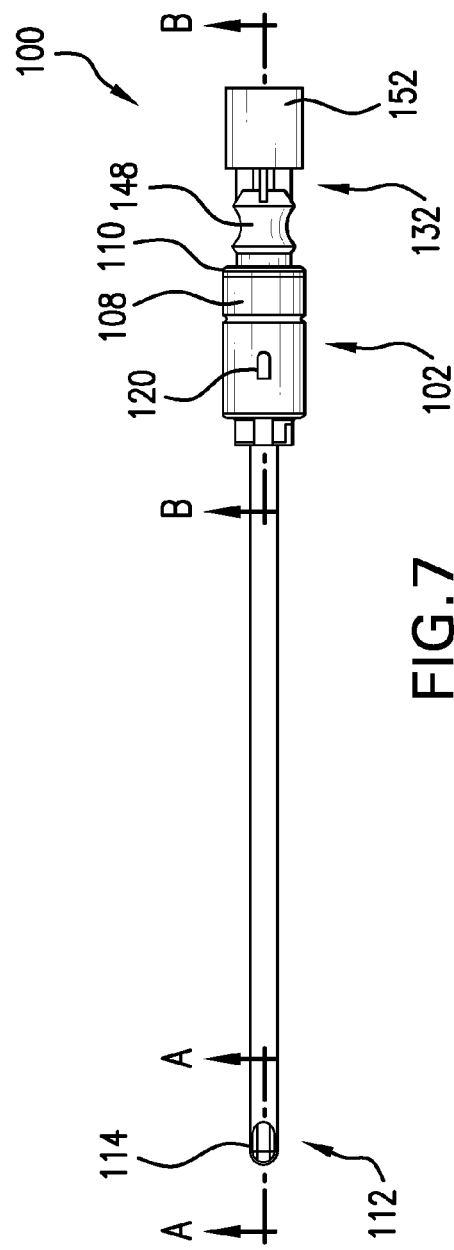
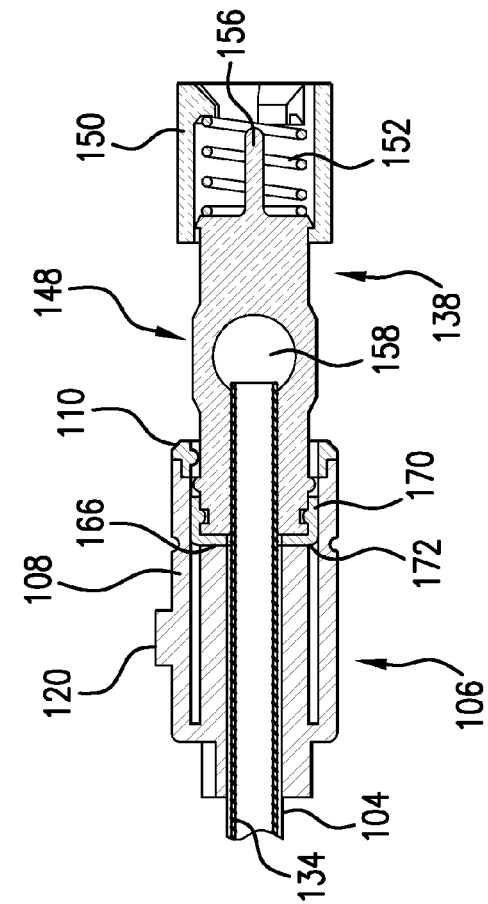
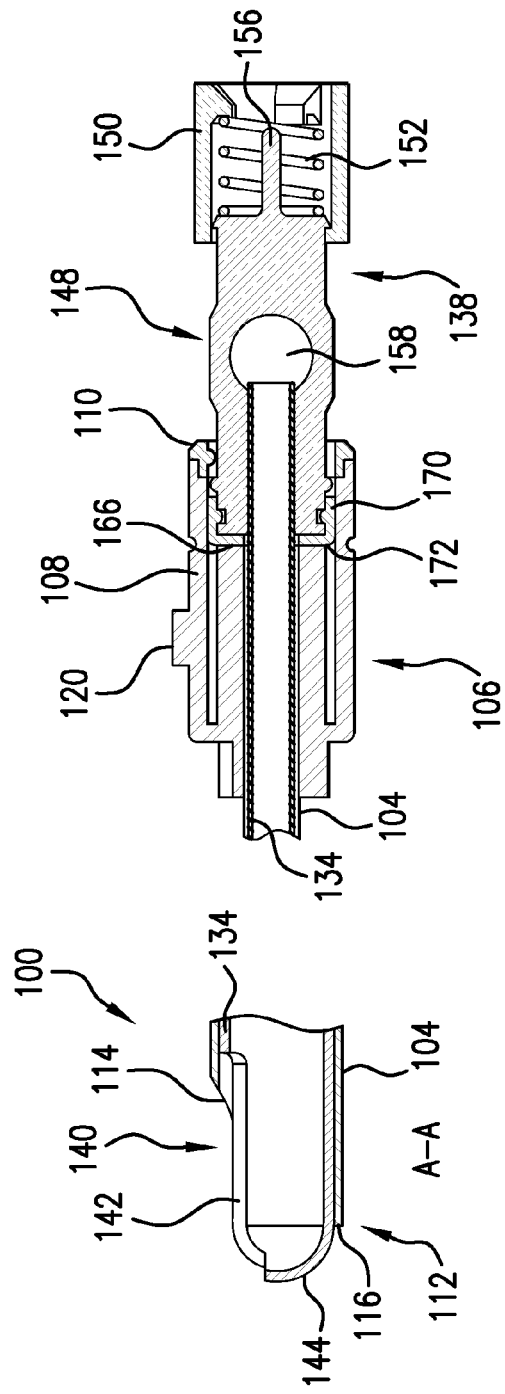

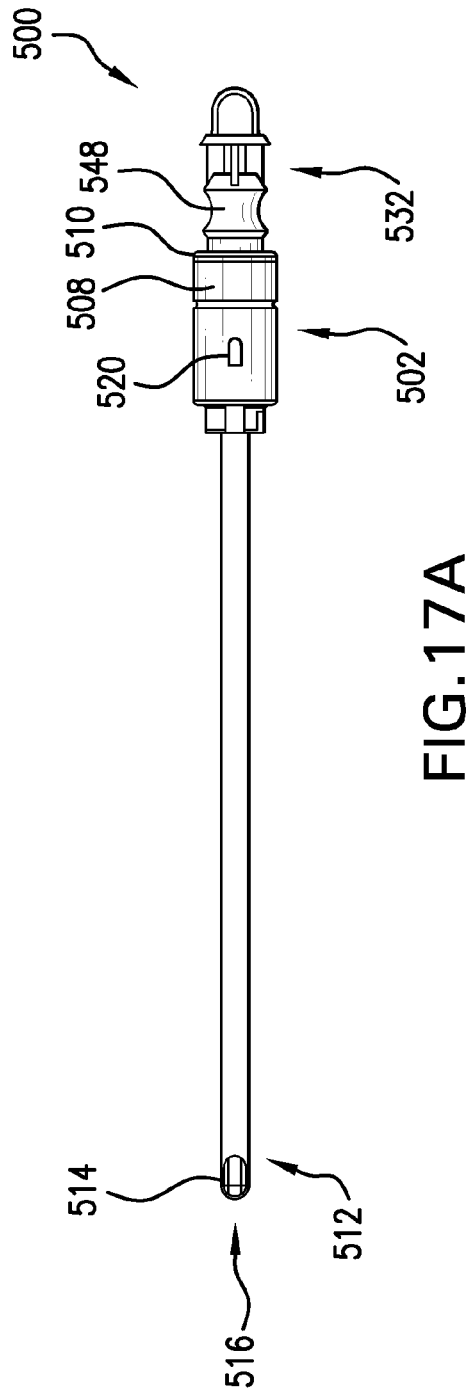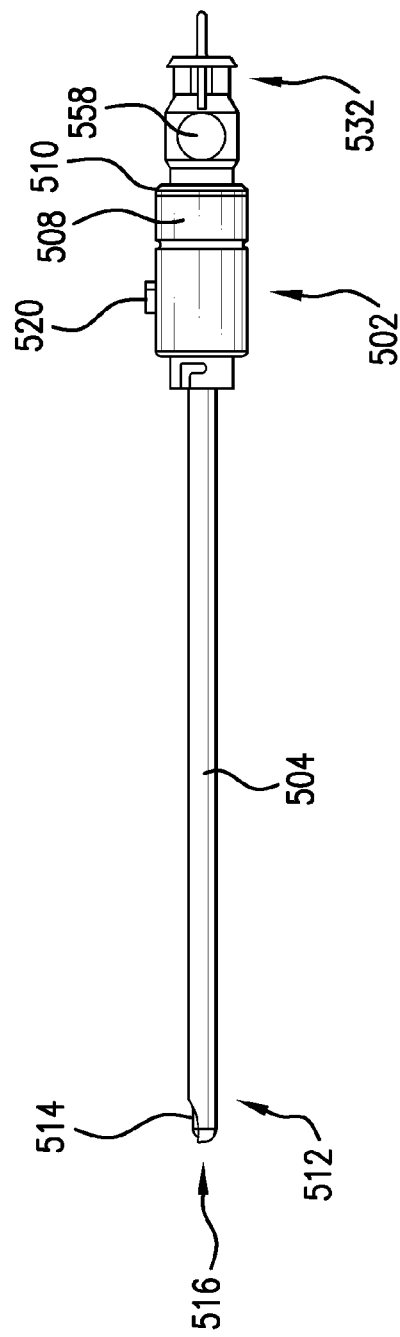
FIG.17A
FIG.17B

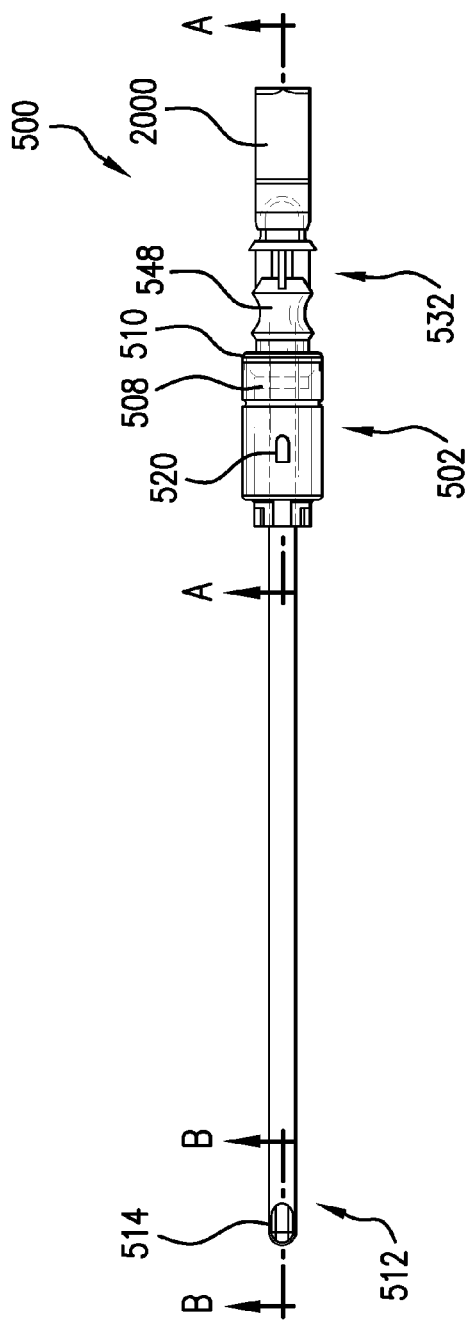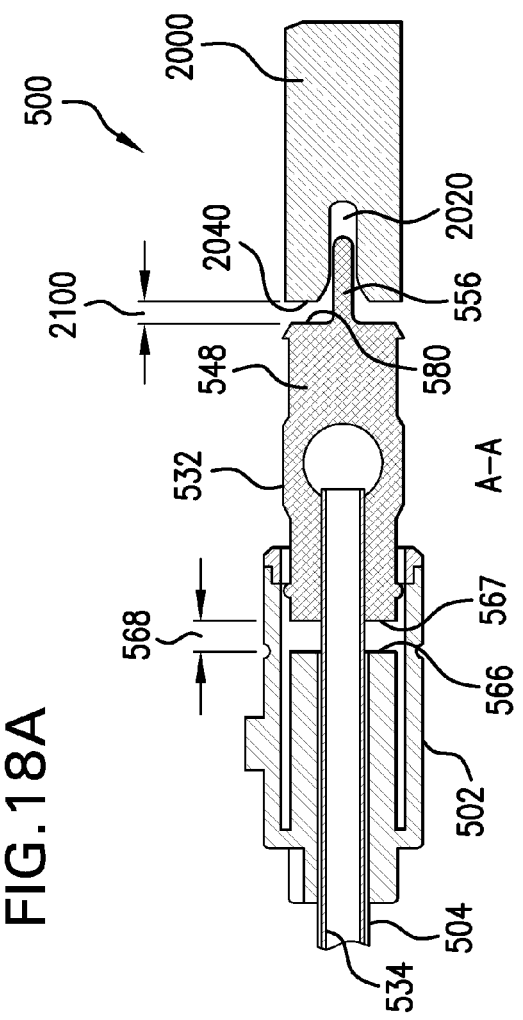

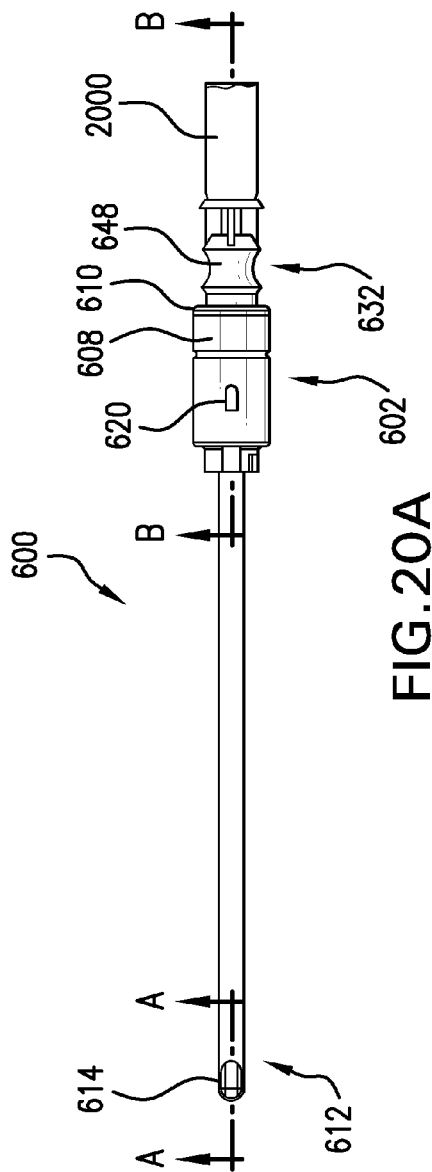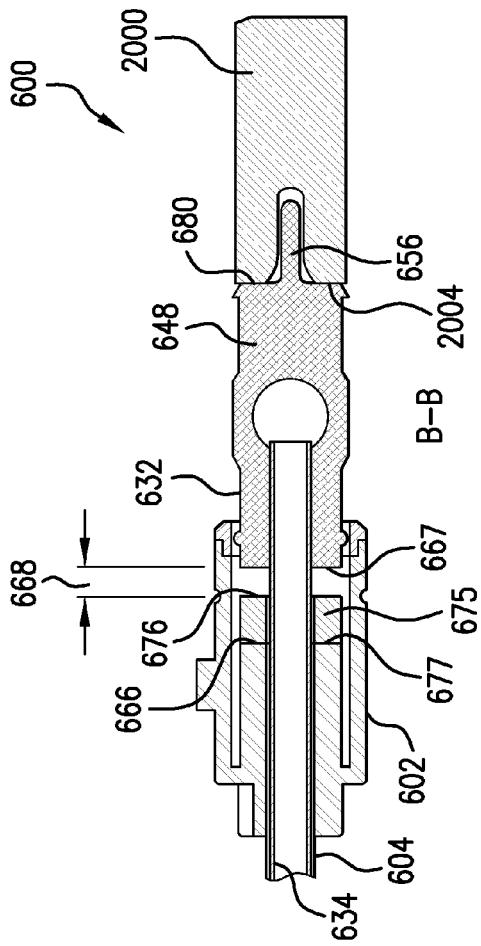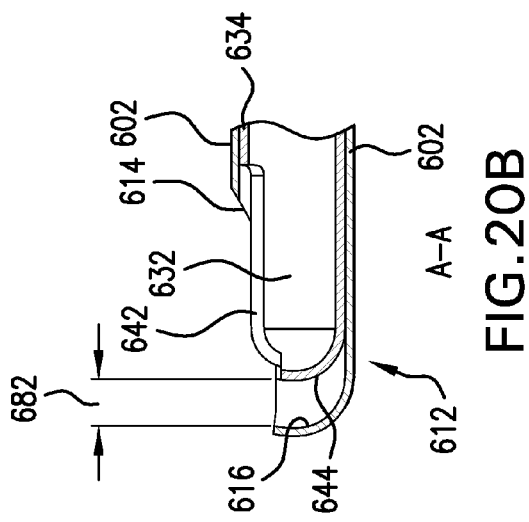

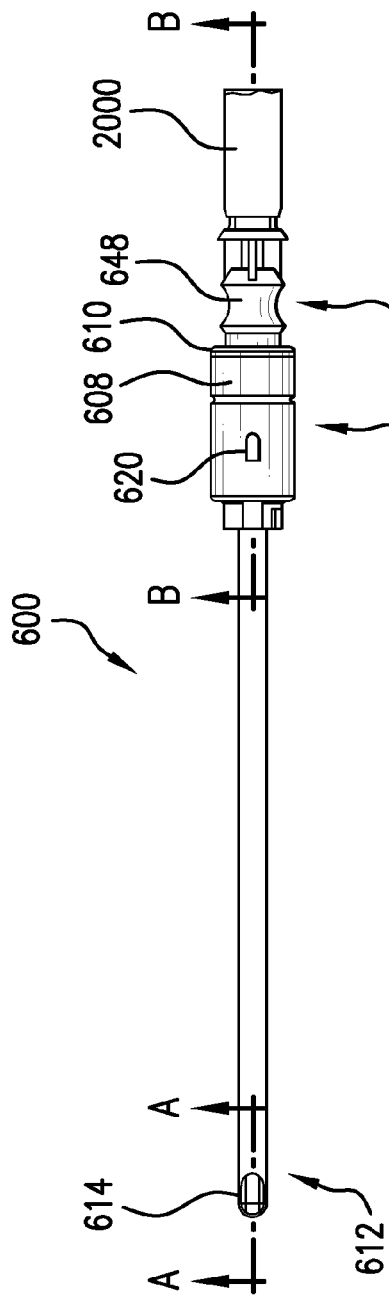
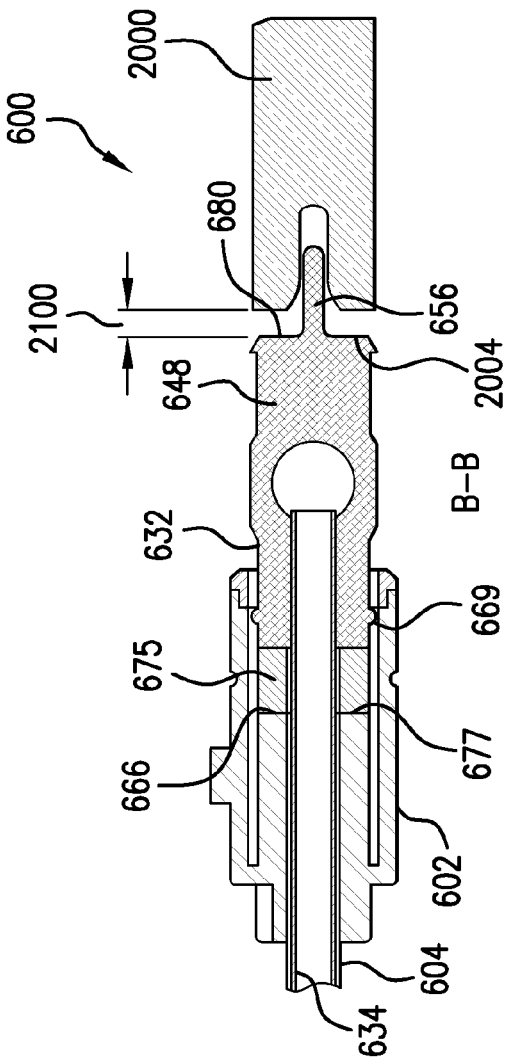
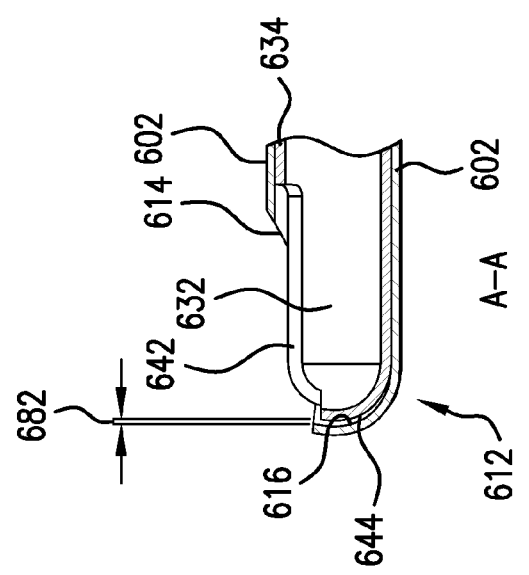
FIG.21A
FIG.21C
FIG.21B

ENDOSCOPIC CUTTING INSTRUMENTS HAVING IMPROVED CUTTING EFFICIENCY AND REDUCED MANUFACTURING COSTS

PRIORITY

This application claims is a divisional of U.S. patent application Ser. No. 12/175,428, filed Jul. 17, 2008, which, in turn, claims the benefit of U.S. Provisional Application Ser. No. 60/964,590, filed Aug. 13, 2007, and U.S. Provisional Application Ser. No. 61/011,828, filed Jan. 22, 2008.

U.S. patent application Ser. No. 12/175,428 is also a continuation-in-part of U.S. patent application Ser. No. 11/634,102, filed Dec. 6, 2006, now U.S. Pat. No. 7,666,200, issued Feb. 23, 2010, which, in turn, claims the benefit of U.S. Provisional Application Ser. No. 60/831,986, filed Jul. 19, 2006.

The contents of all cited priority applications are hereby incorporated by reference herein in their entirety.

TECHNICAL FIELD OF THE INVENTION

The present invention relates generally to the field of endoscopic tissue resection and powered surgical instruments for use therein, more particularly to minimally invasive endoscopic cutting instruments having improved cutting efficiency and reduced manufacturing costs. In particular, the present invention teaches the elimination of or modification to the distal bearing surface of such instruments, thereby eliminating or substantially reducing the high localized heating and galling that is characteristic of conventional endoscopic shaver devices.

BACKGROUND OF THE INVENTION

In contrast to conventional surgery, which requires a relatively large incision in order to gain access to a surgical site within a body, endoscopic procedures utilize natural passages, or, alternatively, involve the formation of very small portals to gain access to the surgical site of interest. Accordingly, an endoscopic procedure is often referred to as minimally invasive surgery. One advantage of performing endoscopic surgery is that since the portions of the body that are cut are reduced, the portions of the body that need to heal after the surgery are likewise reduced. Still another advantage of endoscopic surgery is that it exposes less of the interior tissue of the body to the open environment. This minimal opening of the body lessens the extent to which its internal tissue and organs are open to infection.

Advancements in this field of "closed" surgery, such as arthroscopy and, more generally, endoscopic surgery, have led to the creation of numerous minimally invasive surgical cutting instruments. As noted above, in closed surgery, access to the surgical site is gained via one or more portals. As such, the instruments used in the surgical procedure must be sufficiently flexible, smooth and elongated to permit the distal ends of the instruments to reach the surgical site with minimal trauma to neighboring tissues. One end of the instrument, often referred to as the "distal end", is designed to be positioned at the surgical site. The opposed end of the instrument, often referred to as the "proximal end", extends out of the patient's body. The distal end of the instrument is typically provided with some type of working head designed to manipulate the tissue against which it is placed whereas the proximal end of the instrument is provided with a mechanism for the user to remotely control the working head.

Surgical cutting instruments for use in closed surgery—often referred as endoscopic "shavers"—are typically composed of a pair of concentrically disposed, close-ended, generally tubular members, more typically an elongated outer tubular member terminating in a distal opening or "cutting window", an aperture situated in the distal end, on the distal end side wall, or both, and an elongated inner tubular member, slidably and concentrically disposed in the outer tubular member, whose distal end is disposed adjacent the cutting window of the outer tubular member. The distal end of the inner tubular member typically has a surface or edge for engaging tissue via the distal opening in the outer tubular member and cooperates with the opening to shear, cut or trim tissue, a process often referred to as "resection". For example, the inner tubular member may be rotatably driven about its axis from its proximal end by a handpiece having a small electric motor which is controlled by one or more finger actuated switches on the handpiece, one or more foot switches on a console supplying power to the handpiece, or some other analogous control means. Cut tissue can then be aspirated through the hollow lumen of the inner tubular member to be collected via a vacuum tube communicating with the handpiece. The distal end of the inner tubular member can be provided with a number of dimensions or configurations, depending upon the surgical procedure to be performed. Similarly, the opening in the distal end of the outer tubular member may be adapted to cooperate with the particular configuration of the distal end of the inner tubular member. For example, the inner and outer tubular members can be configured to produce side cutting or end cutting, or a combination of the two, to cut soft or bony tissues or combinations thereof. These various configurations are generally referred to in the art as "shaver blades".

The cutting windows of a shaver each have perimeters composed of two relatively longitudinal, straight or curvilinear edges connected at their proximal ends and distal ends by two relatively transverse edges. The configuration of the longitudinal edges, and to a lesser extent the transverse edges is determined by the intended use of the shaver. For instance, shavers intended for use on soft tissue will be provided with cutting windows configured for increased resection efficiency but relatively low resistance to deformation since the cutting forces are typically low. Conversely, those shavers intended for use on tough tissue, such as meniscus or vertebral discs, will be provided with a greater resistance to deformation since the cutting forces are quite high.

Resection of tissue by a shaver blade is typically accomplished by the cooperative interaction between the sharp beveled edges of the inner and outer cutting windows. As the inner and outer windows come into alignment, vacuum within the lumen of the inner member aspirates tissue into the opening formed. Continued rotation of the inner member causes the inner cutting edges to approach the outer cutting edges. Tissue in the cutting window between the inner and outer edges is either trapped between the edges or ejected from the window. Tissue trapped between the edges is either cut by the edges as they approach each other or torn by the cutting edges as they pass and rotate away from each other. The resected tissue is then aspirated from the site through the inner lumen of the inner member.

Resection efficiency can be improved by decreasing the relative portion of the material that is ejected from the window, and increasing the portion that is trapped between the edges and resected. Decreasing the relative portion ejected from the window can be achieved through the use of sharper cutting edges. Illustrative means for increasing the sharpness of the cutting edge include decreasing the included angle of the cutting edge, decreasing the edge radius, and decreasing the roughness of the surfaces over which tissue must slide during resection. For example, U.S. Pat. No. 5,843,106 (Heisler) discloses a shaver with increased resection efficiency produced by an outer cutting window configuration having "sharpened" low included-angle cutting edges. The relative portion of tissue ejected from the window during closure may also be decreased by adding teeth to either the inner cutting edges or outer cutting edges or both. Shavers having inner cutting edges with teeth are described in the art, for example in U.S. Pat. Nos. 5,217,479 (Shuler) and 5,269,798 (Winkler), each of which disclose shavers having inner cutting edges with teeth, such teeth being formed by a "through-cutting" process, such as wire electrical discharge machining (wire EDM), or by grinding. Teeth so formed are efficient at retaining tissue within the window so that it can be cut by the low included angle outer cutting edges as the inner and outer edges converge. The inner cutting edges do little cutting since the teeth form a very large included angle cutting edge.

The Cuda™ by Linvatec Corporation (Largo, Fla.) and the Tomcat™ by Stryker Corporation (Kalamazoo, Mich.) each have teeth on both the inner and outer cutting edges, the edges being formed by a two-dimensional, through-cutting process such as grinding or wire EDM. The edges formed have large included angles, a geometry that is inefficient for cutting tissue. Shavers having these two-dimensionally shaped teeth on the inner and outer cutting edges separate tissue principally by tearing as the edges pass each other when the cutting window is closed. Such tearing is undesirable since the torn tissue frequently becomes trapped in the gap between the inner and outer tubular members, thereby causing clogging. This problem is specifically addressed in U.S. Pat. No. 6,053, 928 (Van Wyk et al.), which discloses a shaver having a plurality of teeth on the laterally opposed cutting edges of an outer window, the cutting edges being symmetrical when viewed in a plane normal to the axis of the tube. The cutting edges are formed so that, when viewed in any such plane, the edges have low included angles, in the valleys between the teeth as well as the teeth. The Great White™ shaver by Linvatec, constructed in accordance with the principles of the '928 patent, is very efficient at resecting tissue and experiences reduced clogging due to the sharpness of the outer cutting edges.

When a shaver is used with a constant rotation imparted to the inner member, tissue in close proximity to the window is sucked into the window and either resected or ejected from the window in the manner previously herein described. Tissue that is ejected from the window, or the remaining tissue adjacent to a resected portion, is swept in the direction of the rotation. When the cutting window is opened again by the rotation of the inner member, the amount of tissue which will be pulled into the window by vacuum in the inner lumen is diminished from that of the previous opening event because of this directional "set" of the tissue. That is, because the tissue is already preferentially oriented in the direction of the rotation of the approaching inner cutting edge, it is difficult for that inner cutting edge to get sufficient "bite" to retain the tissue in the cutting window for resection. Because of this, arthroscopic shavers are generally used in an "oscillate" mode when cutting tissue. In this mode the inner is rotated in one direction for a predetermined number of revolutions, whereupon its rotation is reversed for the same predetermined number of revolutions. The inner cutting edges approach the tissue from alternating directions thereby greatly increasing the relative portion of tissue that is sucked into the window and is resected rather than ejected.

As noted above, a conventional (prior art) shaver blade assembly is composed of a stationary outer assembly and an inner assembly. The inner assembly is typically composed of a generally tubular member with a closed distal end and a proximal-end hub configured for removable coupling a drive mechanism of a powered handpiece so as to transmit rotational motion from the handpiece to the distal end of the inner assembly. The outer assembly is typically composed of a generally tubular member with a closed distal end and a proximal hub means for removably mounting the shaver blade assembly in a powered handpiece. An elastic member transmits an axial force distally on the inner assembly so that contact is maintained between the outer surface of the distal end of the inner member and the inner surface of the distal end of the outer member, the surfaces together functioning as a bearing. In some shaver systems, the elastic member is a spring affixed to the hub of the inner assembly. In other systems, the elastic member is a spring in the handpiece in which the shaver is mounted. The distal bearing surfaces are spherical on most (almost all) shavers, although shavers with other shapes are produced for specialized purposes. The radius of the spherical inner surface of the outer member is slightly larger than that of the spherical external surface of the inner member. The application of the axial force to the inner member by the elastic member creates quite high Herzian contact stresses at the bearing surfaces. Since shavers are used with rotational speeds as high as 5,000 rpm, chafing or galling of these surfaces is frequently a problem. To prevent galling, the materials of the inner and outer distal ends are carefully selected and the components hardened and machined to very precise shapes, frequently with form tolerances of as little 0.0002 inches. The surface finishes of the bearing surfaces are also critical since irregularities in the surfaces can lead to high localized stresses which result in galling of the surfaces during use. Galling of the bearing surfaces during use creates metallic debris which can be deposited into the surgical site, with negative consequences to the patient. In severe cases, galling may cause welding of the inner and outer members so as to make the shaver unusable. As a result, some manufacturers coat the inner member bearing surface with a gall-resistant metallic material, while others make the distal end of the inner member from a gall resistant alloy. In any event, galling and metallic debris created by shaver blades is still a frequent problem since inspection of the inner surface of the outer member is very difficult and minor manufacturing abnormalities can create surfaces which are not to specification. Because of these and other factors, forming of the inner and outer distal end bearing surfaces is a significant portion of the shaver blade manufacturing costs.

Closely related to arthroscopic shavers is a category of devices known in the art as arthroscopic burs, which are used for resecting bone. Burs differ from shavers in that the inner member has multiple cutting edges arranged on a rotating element (the bur head), with cutting achieved solely by the inner cutting edges. While shavers cut by cooperative interaction of the inner and outer cutting edges, burs cut with the inner edges only. Also, shavers use a vacuum to draw tissue into a cutting window for resection while burs use suction only to remove debris from the surgical field. Burrs are ineffective for cutting soft tissue. Typical burrs are the Spherical Burr, Oval Burr, Cyclone Burr, and Vortex Router by Conmed Corporation (Utica, N.Y.). The axial bearing surface of a burr is not at the distal tip since the outer tube end is not closed, but rather is proximally located and is formed by a dissimilar material pair formed by a proximal surface of the outer hub assembly and a distal surface of the inner hub assembly. Burrs are ineffective for resecting soft tissue.

The Helicut™ burr by Smith and Nephew Incorporated (Andover, Mass.), and the Lightning™ by Conmed Corporation are specialty burrs which cut both soft tissue and bone. The instruments have a helical rotational inner member with two cutting edges, and an open-ended outer member with edges which cooperatively resect soft tissue with the edges of the inner member. The resected tissue is removed from the site by the action of the helical inner as well as by a vacuum applied to the proximal end of the outer member. The Helicut and Lightning are unique in that they resect both bone and soft tissue, and do not have a tubular inner member. The axial bearing surface of these devices is not at the distal tip since the outer tube end is not closed, but rather is proximally located and is formed by a dissimilar material pair formed by a proximal surface of the outer hub assembly and a distal surface of the inner hub assembly. The resection efficiency of these blades having a helical inner is quite low when cutting soft tissue since there are no teeth on the inner or outer member to aid in preventing tissue ejection as the cutting edges approach.

Arthroscopic cutting instruments may be divided into two categories: those with tubular inner members which have an axial bearing formed by the closed distal ends of the inner and outer tubes, and those which do not have tubular inner members and whose axial bearings are proximally located.

Thus, there are a number of commercially available embodiments of powered endoscopic cutting instruments. Nevertheless, despite the above described improvements, there remains a clear need in the art to increase the efficiency of endoscopic cutting instruments and shaver blades and to reduce their manufacturing costs. The present invention is directed to these needs.

SUMMARY OF THE INVENTION

In view of the foregoing, it is a primary object of the present invention to provide an endoscopic shaver assembly having improved cutting efficiency and reduced manufacturing costs.

In the context of the present invention, endoscopic cutting instrument is characterized by an elongated inner member axially slidable and rotatably situated within an elongated stationary outer member, wherein both inner and outer members have at their distal ends cutting apertures which cooperate to resect tissue during endoscopic surgical procedures. As noted above, prior art shavers with tubular inner and outer distal assemblies maintain axial positioning between the assemblies by applying a distal force to the inner assembly so that the closed distal end of the inner member maintains contact with the distal inner surface of the outer assembly. The two surfaces together form a distal bearing, with the distal force being supplied by a compression spring, either a part of the shaver assembly or the handpiece into which the shaver is removably mounted. Contact stresses (Hertzian in the case of spherical surfaces) at the distal bearing surfaces can be high and can cause galling and generation of metallic debris if the surfaces are improperly designed or formed. It is a primary goal of the instant invention to eliminate this distal bearing, or provide means for making the contact at the distal bearing intermittent so that surfaces do not undergo high localized heating and galling.

In one embodiment, this goal is achieved by means of an open-ended tube. For example, the distal end of the outer tube, rather than being closed as is characteristic of conventional endoscopic shavers, is open while the distal end of the inner tube is closed. The opposite configuration, wherein the distal end of the inner tube is open while the distal end of the outer tube is closed, is also contemplated. In this configuration, the axial bearing then becomes proximally located. By eliminating distal bearing surfaces, the present invention provides a substantial reduction in manufacturing costs. However, in addition to eliminating distal bearing forces and reducing manufacturing costs associated therewith, removing the closed distal end of one of the tubular members can also improve cutting efficiency. For example, by removing the closed distal end of the outer tube that is typical of prior art shavers, one can provide additional tissue access to the inner cutting window.

In an alternate embodiment, this goal is achieved by means of a free-floating inner member. It was discovered herein that allowing the inner member to axially "float" resulted in an increase in the resection efficiency of a shaver. Specifically, with a free floating inner member, the teeth on the inner cutting edge able to preferentially find regions of least resistance (i.e., the "sweet spot" in which the cutting edge is able to most easily penetrate tissue) to thereby minimize the ejection of tissue from the cutting window. In contrast to prior art shavers, in which the position of teeth on the cutting edge is fixed relative to the position of the outer member and tissue in proximity therewith such that the inner and outer edge teeth intersect the tissue repeatedly in a given location, the teeth on the endoscopic shaver of the present invention are able to contact the tissue in random locations so as to enhance tooth penetration. A shaver formed in accordance with the principles of the present invention does not have a bearing, but rather stops which limit axial travel of the inner member. Elimination of the bearing with its associated high manufacturing costs allows the shaver to be produced at low cost. Elimination of the distal bearing, with its associated proclivity for generation of metallic debris by galling of the bearing surfaces, also reduces metallic debris.

In this alternate embodiment, the distal axial force applied to the inner assembly and thus the corresponding the distal bearing surface is eliminated by removing or reducing the axial constraints on the inner member that are characteristic of conventional endoscopic shavers, allowing it to travel unrestricted within predetermined limits. For example, proximal movement of the inner assembly may be limited by one or more coordinating features in the handpiece, the inner hub and/or in the outer hub. Distal movement of the inner assembly may be limited by contact between the outer surface of the inner assembly distal end and the inner surface of the outer assembly distal end, the surfaces functioning as a stop rather than a bearing, or by contact between the proximal surface of the outer member hub and the distal surface of the inner member hub, with or without the inclusion of a proximally positioned spacer positioned therebetween. When the distal limit is due to a spacer between the inner and outer hubs, it is preferable to provide a predetermined minimum gap between the outer surface of the inner assembly distal end and the inner surface of the outer assembly distal end, thereby preventing contact therebetween that may result in unintended heating or galling.

In yet another embodiment, the distal bearing is replaced by a proximal bearing, the bearing consisting of a wear-resistant spacer between the inner and outer hubs. A distal axial force applied by a spring maintains contact between the hubs and the spacer. A gap is maintained between distal outer surface of the inner distal member and the inner surface of the closed distal end of the outer distal member.

In yet a further embodiment, the spacer of the previous embodiments is replaced by a cam and follower affixed to the inner and outer hubs. The cam and follower cooperatively determine the axial position of the inner assembly within the outer assembly. In one form, contact between the cam and follower is constant so that the bearing is always formed by the cam and follower surfaces and a predetermined gap is maintained at the distal end. In another form the distal bearing surfaces are in contact except when the inner assembly is displaced proximally by cooperative interaction between the cam and follower. In a preferred embodiment, the inner assembly is displaced axially twice in each revolution of the inner, each displacement being 20 degrees or more of rotational angle. Other displacement frequencies and durations may be used. Periodic separation of the distal bearing surfaces allows cooling of the contacting surface portions, and contamination of these portions by saline solution and tissue. Contaminants on the bearing surfaces act as lubricants minimizing or eliminating galling and the generation of metallic debris.

It is, accordingly, an object of the present invention to reduce manufacturing costs by the elimination of or modification to the distal end axial bearing.

It is further an object of the present invention to provide a shaver having reduced opportunity for galling and metal shedding by eliminating the distal end axial bearing.

It is also an object of the present invention to facilitate a shaver manufacture through the elimination of critical distal bearing surface features which, under conventional practices, must be formed to close tolerances and which are difficult to inspect.

It is also an object to provide an endoscopic shaver assembly with high resection efficiency, wherein tissue ejection is reduced by means of an axially floating inner member which allows the inner cutting edge to more efficiently engage tissue, or wherein tissue access to the cutting window is increased through the removal of the outer tube closed end, or a combination of the two.

Accordingly, in one embodiment, the present invention provides an endoscopic surgical assembly characterized by a concentrically disposed elongated tubular inner and outer members, each of said elongated members comprising a coordinating hub disposed at its proximal end, a laterally disposed cutting aperture at its distal end, and a central lumen extending therebetween, said inner member being sized to be slidably received within the lumen of said outer member, wherein when said inner and outer hubs are connected, axial displacement between the inner and outer members is fixed and the respective cutting apertures of said inner and outer members are aligned to permit cooperative resection of tissue in contact therewith, further wherein (a) the inner member comprises a distally facing open end while the distally facing end of the outer member comprises a closed surface, or (b) the outer member comprises a distally facing open end while the distally facing end of the inner member comprises a closed surface.

In an alternate embodiment, the present invention provides an endoscopic surgical assembly characterized by concentrically disposed tubular elongated inner and outer members, each of said elongated members comprising a coordinating hub disposed at its proximal end, a laterally disposed cutting aperture at its distal end, and a central lumen extending therebetween, said inner member being sized to be slidably received within the lumen of said outer member, wherein axial force on said inner member is eliminated, thereby permitting said inner member to move axially within predetermined limits, further wherein when said inner and outer hubs are connected the respective cutting apertures of said inner and outer members are aligned to permit cooperative resection of tissue in contact therewith but the distal ends of the inner and outer members do not form a distal bearing surface.

In yet another embodiment, the present invention provides an endoscopic surgical assembly characterized by concentrically disposed elongated tubular inner and outer members, each of said elongated members comprising a coordinating hub disposed at its proximal end, a laterally disposed cutting aperture at its distal end, and a central lumen extending therebetween, said inner member being sized to be slidably received within the lumen of said outer member, wherein:

(a) the inner member hub includes an elastic member that transmits an axial force distally on said inner member so as to constrain proximal movement thereof;

(b) the proximal end of the outer member hub is characterized by an outer collar concentrically disposed about an inner stem, said assembly further comprising an annular spacer element positioned between the proximal end of the inner stem and the distal end of the inner member hub so as to prevent direct contact therebetween; and (c) when said inner and outer hubs are connected the distal ends of the inner and outer members do not form a distal bearing surface.

The above assemblies may be modified to include or used in connection with one or more aspiration and/or irrigation means. They may further be modified to include or used in connection with conventional powered handpiece assemblies and/or drive mechanisms to facilitate operation. The present invention accordingly provides methods of using the endoscopic surgical assemblies of the present invention in the field of "closed" surgery, such as arthroscopy and, more generally, endoscopic surgery.

In a preferred embodiment, the concentrically disposed inner and outer members of the endoscopic surgical assembly comprise concentric tubes provided with laterally disposed cooperating cutting windows. In one preferred embodiment, the inner member is provided with a closed end while the outer tube is provided with an open end. In an alternate preferred embodiment, it is the inner member that is open ended while the outer member is closed.

In a preferred embodiment, each cutting window is provided with a perimeter comprised of two longitudinal cutting edges and at least one, possibly two transverse cutting edges. The cutting edges may be linear, curvilinear or a combination thereof, thereby providing the cutting window with an overall shape that is regular or irregular, symmetrical or asymmetrical shape. Examples of suitable cutting window shapes include, but are not limited to, circles, ellipses, polygons such as rectangles, squares, rhomboids, trapezoids, and the like, as well as portions and combinations thereof.

While the present invention is not limited to cutting windows of any particular size, shape and dimension, in order to achieve efficient cutting, it is preferable that at least a portion of one or more cutting edges is angled or beveled so as to yield a sharp cutting surface. A suitable included angle for the beveled cutting edges preferably ranges from 15 to 70 degrees, and more preferably ranges between 20 and 50 degrees.

These and other objects are accomplished in the invention herein described, directed to an endoscopic shaver blade having improved cutting efficiency. Further objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims.

BRIEF DESCRIPTION OF THE DRAWINGS

FIG. 3 is a plan view of the prior art arthroscopic shaver blade assembly of FIG. 1.

FIG. 4 is a side elevational sectional view of distal portion of the arthroscopic shaver blade assembly of FIG. 1, at location B-B of FIG. 3.

FIG. 5 is a side elevational sectional view of the proximal portion of the arthroscopic shaver blade assembly of FIG. 1, at location A-A of FIG. 3.

FIG. 7 is a plan view of the open-ended shaver assembly of FIG. 6.

FIG. 8 is a side elevational sectional view of the distal portion of the open-ended shaver assembly of FIG. 6, at location A-A of FIG. 7.

FIG. 9 is a side elevational sectional view of the proximal portion of the open-ended shaver assembly of FIG. 6, at location B-B of FIG. 7.

FIG. 17A is a plan view of a free-floating shaver assembly formed in accordance with the principles of the present invention.

FIG. 17B is a side elevational view of the free-floating shaver assembly of FIG. 17A.

FIG. 18A is a plan view of the free-floating shaver blade assembly of FIG. 17, depicting the inner assembly in its most distal position.

FIG. 18B is a side elevational sectional view of the distal portion of the free-floating shaver assembly of FIG. 17, at location B-B of FIG. 18A.

FIG. 18C is a side elevational sectional view of the proximal portion of the free-floating shaver assembly of FIG. 17, at location A-A of FIG. 18A.

FIG. 20A is a plan view of an alternate embodiment of a free-floating shaver assembly formed in accordance with the principles of the present invention, depicting the inner assembly in its most proximal position.

FIG. 20B is a side elevational sectional view of the distal portion of the free-floating shaver assembly of FIG. 20A, at location A-A thereof.

FIG. 20C is a side elevational sectional view of the proximal portion of the free-floating shaver assembly of FIG. 20A, at location B-B thereof.

FIG. 21A is plan view of the free-floating shaver assembly of FIG. 20A, depicting the inner assembly in its most distal position.

FIG. 21B is a side elevational sectional view of the distal portion of the free-floating shaver assembly of FIG. 20A, at location A-A of FIG. 21A.

FIG. 21C is a side elevational sectional view of the proximal portion of the free-floating shaver assembly of FIG. 20A, at location B-B of FIG. 21A.

DETAILED DESCRIPTION OF THE PREFERRED EMBODIMENTS

Figure 1:
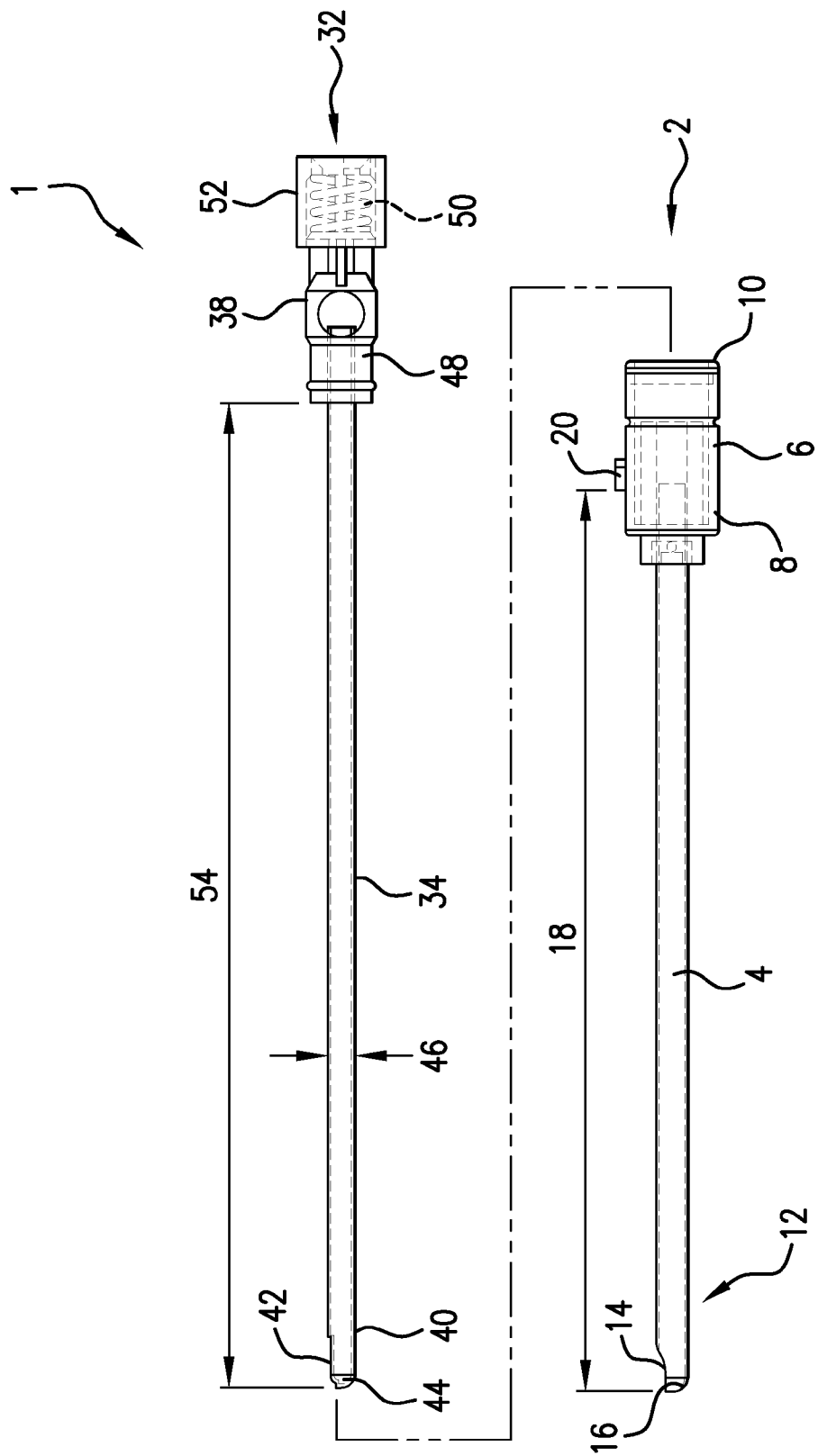
FIG. 1 is a disassembled view of a prior art arthroscopic shaver blade assembly.
Figure 2:
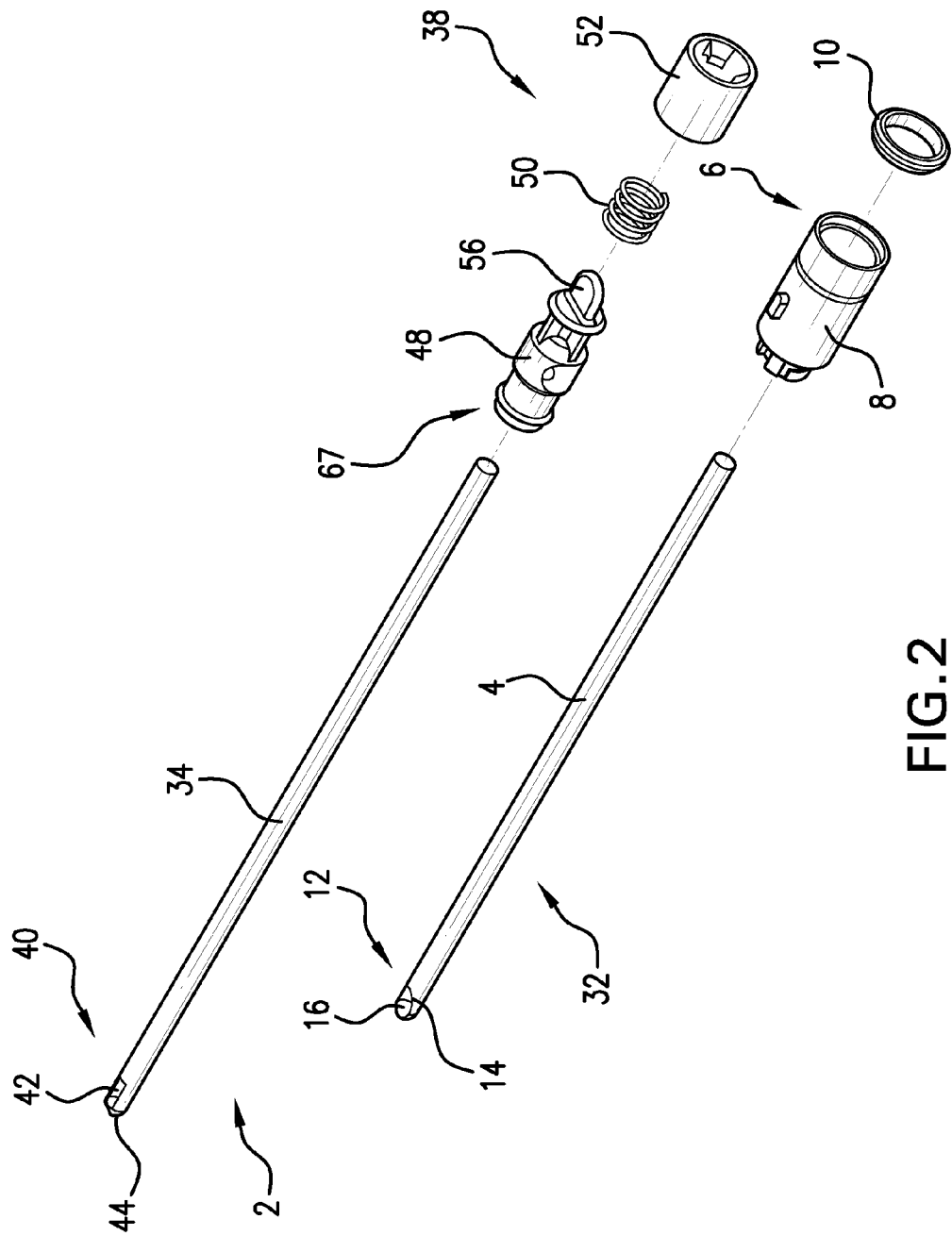
FIG. 2 is an exploded view of the inner and outer assemblies of the prior art arthroscopic shaver blade assembly of FIG. 1.
Figure 6A:
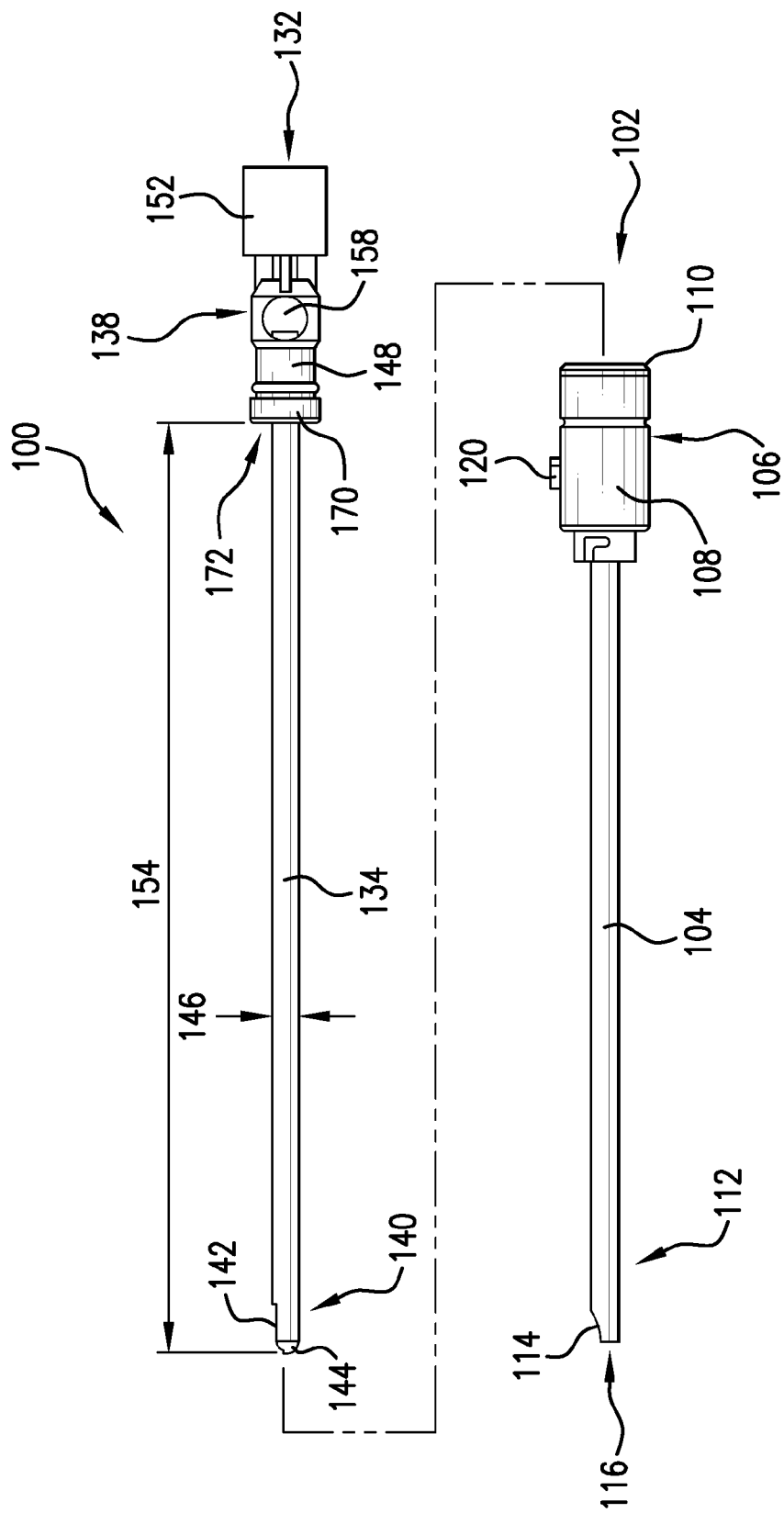
FIG. 6A is a disassembled view of an open-ended shaver blade assembly formed in accordance with the principles of the present invention.
Figure 6B:
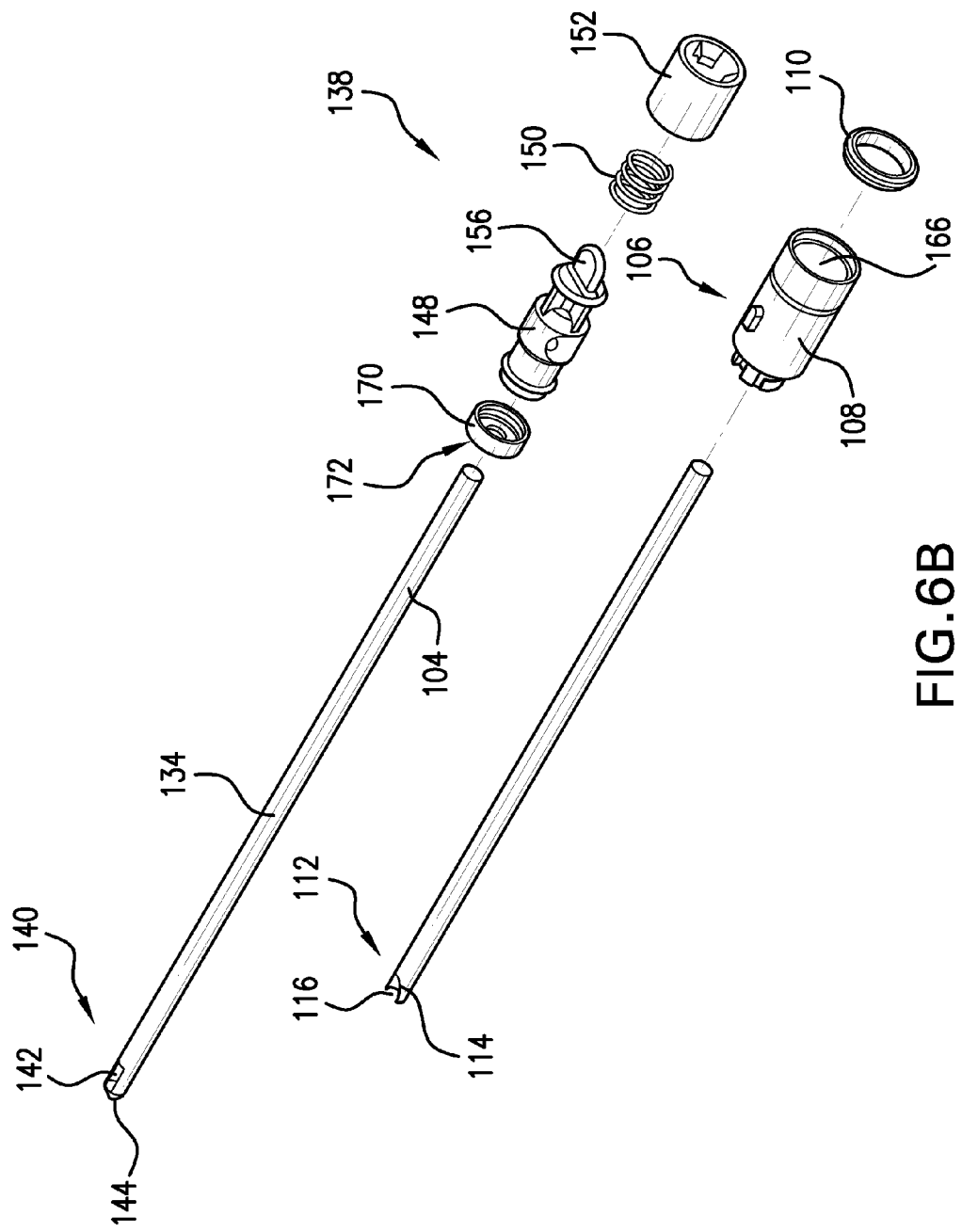
FIG. 6B is an exploded view of the inner and outer assemblies of the open-ended shaver assembly of FIG. 6A.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which the present invention belongs. However, in case of conflict, the present specification, including definitions, will control.

In the context of the present invention, the following definitions apply:

The words "a", "an" and "the" as used herein mean "at least one" unless otherwise specifically indicated. Thus, for example, reference to a "cam lobe" is a reference to one or more cams and equivalents thereof known to those skilled in the art, and so forth.

The term "proximal" as used herein refers to that end or portion which is situated closest to the user of the device, farthest away from the target surgical site. In the context of the present invention, the proximal end of the inventive device includes the handpiece region.

The term "distal" as used herein refers to that end or portion situated farthest away from the user of the device, closest to the target surgical site. In the context of the present invention, the distal end of the inventive device includes the respective cutting windows of the inner and outer tubular members.

The term "rotational" as used herein refers to the revolutionary movement about the center point or longitudinal axis of the device. In the context of the present invention, rotation of the elongated inner tubular member relative to the elongated outer tubular member, which typically is held in a stationary position, results in relative rotation of their respective cutting apertures which coordinate to resect target tissue within the surgical site of interest.

The term "axial" as used herein refers to the direction relating to or parallel with the longitudinal axis of the device. In the context of the present invention, relative axial movement between the elongated outer tubular member and the elongated inner tubular member slidably received therein results in improved cutting efficiency. The present invention contemplates the combination of relative axial displacement and relative rotational motion to enhance cutting efficiency. Means for automating such axial and rotational movement are described in U.S. Patent Publication No. 2008-0021487-A1 to Heisler (hereinafter USPP '487), the entire contents of which are incorporated herein by reference. Specifically, where appropriate, the endoscopic cutting instruments of the present invention may be modified to include the means for automating axial movement with rotation motion described in USPP '487.

The present invention makes reference to "bearings" and "bearing surfaces". The terms "bearing" and "bearing surface" refer to elements and surfaces that constrain relative motion between two parts, typically rotation or linear movement. Bearings may be classified broadly according to the motions they allow and according to their principle of operation as well as by the directions of applied loads they can handle. In the context of the instant invention, the bearing surface at issue arises at the interface between the outer surface of the spherical distal end of the tubular inner member of a conventional shaver blade assembly and the corresponding inner surface of the spherical distal end of the tubular outer member of the conventional shaver blade assembly.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal.

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to arthroscopic shaver blade assemblies, it is readily apparent that the teachings of the present invention may be applied to other minimally invasive cutting instruments and are not limited to arthroscopic uses alone. As such, methods and materials similar or equivalent to those described herein can be used in the practice or testing of the present invention.

Prior Art Shavers

FIGS. 1 through 5 depict a conventional prior art arthroscopic shaver blade assembly 1 having an outer member 2, having an elongate tubular distal portion 4, typically formed from a rigid material such as metal or hard plastic, and a proximal hub portion forming a hub assembly 6 suitable for mounting in a shaver handpiece. Outer member hub assembly 6 includes a hub 8 and retainer 10. Tubular portion 4 includes a distal portion 12 in which is formed cutting window 14 and spherical inner distal surface 16. Distance 18 extends from the distal end of key 20 of hub 8 to the distal-most point of spherical inner surface 16. Shaver blade assembly 1 also includes an inner member 32, having an elongate tubular distal portion 34, which, like the tubular portion of the outer member is also typically formed from a rigid metallic or polymeric material, and a proximal hub portion forming a hub assembly 38 suitable for transmitting rotational motion to inner member 32 by means of an external handpiece (not shown). Tubular portion 34 includes a distal portion 40 in which is formed cutting window 42 and a distal spherical surface 44. Diameter 46 of tubular portion 34 of inner member 32 is slightly less than the diameter of the inner lumen of tubular portion 4 of outer member 2 such that that inner member 12 may be rotatably positioned therein for use. Hub assembly 38 includes hub 48, spring 50 and spring retainer 52. Distance 54 extends from the distal-most surface of hub 48 to the distal-most point on distal spherical surface 44. When mounted in a suitable handpiece, drive tang 56 of hub 48 engages a slot in a driveshaft of the handpiece and spring retainer 52 engages a shoulder on the shaft so as to compress spring 50. Compression of spring 50 ensures that distal spherical surface 44 of inner member 32 is in firm contact with spherical inner surface 16 of outer member 2, surfaces 44 and 16 forming a distal bearing which axially positions inner member 32 within outer member 2. Distances 18 and 54 are selected so that the distal surface 67 of inner hub 48 is displaced from proximal surface 66 of outer hub 8 to form axial gap 68.

During use, tubular portion 34 of inner member 32 is rotated within tubular portion 4 of outer member 2 in an oscillatory manner; that is, the inner member is rotated in one direction a predetermined number of revolutions, stopped, and then rotated in the opposite direction a predetermined number of revolutions. This action is repeated as long as the handpiece in which the shaver blade assembly is mounted is activated. Suction may be supplied to the lumen of tubular portion 34 of inner member 32 by means of a passage 58 in inner hub 48 in communication therewith. Suction draws tissue into contact with, and partially into, the opening formed by angular alignment of cutting windows 14 and 42. Continued rotation of inner member 32 causes tissue to be cut by the cooperative action of the cutting edges of cutting windows 14 and 42.

Additional information on shaver construction and operation may be found in U.S. Pat. Nos. 5,693,063 (Van Wyk et al.), 5,766,199 (Heisler et al.), and 5,843,106 (Heisler), the contents of which are incorporated by reference herein in their entirety.

Prior art shavers like shaver 1 are used at rotational speeds as high as 5,000 rpm. Since there is essentially point contact between the distal spherical surfaces 44 and 16 and the distal bearing formed thereby is subjected to axial force from spring 50, the distal bearing is subjected to high hertzian stresses. When a shaver is used at high speeds, these high hertzian stresses may cause cold welding and galling which, in turn, create metallic debris that may be deposited into the surgical site. Prevention of galling and debris generation is a major concern for shaver blade manufacturers. Spherical surfaces 44 and 16 must have smooth finishes free from irregularities. External spherical surface 44 are most frequently finished by grinding with a grinding wheel having a periphery formed to the radius of the surface. Internal spherical surface 16 is generally formed by reaming. Surfaces 44 and 16 must also be precisely formed so that sliding contact does not occur, for instance, near the tangencies at which the surfaces are joined to the cylindrical surface of the tubes. Rubbing in these tangency areas frequently causes galling since the relative velocity between the surfaces is much higher than at the distal-most point of the radii. Accordingly, surfaces 44 and 16 are generally formed to tolerances of about +/−0.0002 inches. The forming of surfaces 44 and 16 to these close tolerances, and their inspection to ensure that they are to specification are both costly aspects of manufacture.

Prevention of galling at the distal bearing point can also be prevented or minimized through the selection of gall-resistant material for one of the bearing surfaces, through the selection of materials which can be hardened, or through the coating of one of the surfaces with a hard coating such as chromium, or a lubricious coating such as silver or silver with silicon. These methods also significantly increase the shaver blade costs.

Some specialty shaver blade assemblies having tubular inner members have distal bearing surfaces that are not spherical. Such blades, which generally have a flat portion on their closed distal end and are collectively known as "end cutting" shavers, are generally used for trimming meniscus in knees, the corners of the inner cutting windows being useful for penetrating tough meniscal tissue and preventing it from being ejected from the closing cutting window. However, the distal bearing formed by the planar portions of the distal end wall is still subject to the same galling problems as shavers having spherical distal bearing surfaces.

The present invention contemplates the elimination of or modification to the distal bearing surface while retaining the benefits of shavers that utilize vacuum pressure to draw tissue into the cutting window. In this manner, the present invention provides for an improvement in cutting efficiency while at the same time reducing manufacturing costs.

In one embodiment, this goal is achieved by removing the closed distal end of either the inner member or the outer member that is characteristic of conventional shaver assemblies. This embodiment is described in further detail with reference to FIGS. 6 to 16. FIGS. 6 to 12 depict an illustrative example of an "open-ended outer" (referred to herein as "OEO") shaver blade assembly formed in accordance with the principles of the present invention. In contrast, FIGS. 13 to 16 depict an illustrative example of an "open-ended inner" (referred to herein as "OEI") shaver blade assembly formed in accordance with the principles of the present invention.

In another embodiment, this goal is be achieved by mitigating the axial constraints on the inner member that are characteristic of conventional shaver assemblies. This embodiment is described in further detail with reference to FIGS. 17 to 22. FIGS. 17-19 depict one illustrative example of a "free-floating" shaver blade of the present invention. An alternate example of a "free-floating" shaver blade of the present invention, including a proximal spacer element, is depicted in FIGS. 20 and 21. A further alternate example of a modified shaver assembly of the present invention, including the combination of a proximal spacer and coil spring, is depicted in FIG. 22.

Open Ended Shavers

As noted previously, it is a goal of the present invention to eliminate or modify the distal bearing surface of an endoscopic cutting instrument while retaining the benefits of shavers that utilize vacuum pressure to draw tissue into the cutting window, to thereby improve cutting efficiency while at the same time reduce manufacturing costs. As discussed in greater detail below, this goal may be achieved by means of an "open-ended shaver".

Referring now to FIGS. 6 through 9, FIG. 6A depicts shaver 100 formed in accordance with the principles of the present invention. Shaver 100 has an outer member 102, having an elongate tubular distal portion 104, typically formed from a rigid material such as metal or hard plastic, and a proximal hub portion forming a hub assembly 106 suitable for mounting in a shaver handpiece. Hub assembly 106 has a hub 108 and retainer 110. Tubular portion 104 has a distal portion 112 provided with an open distal end 116 and a laterally disposed cutting window 114. Shaver 100 also has an inner member 132, having an elongate tubular distal portion 134, typically formed from a metallic or hard polymer material, and a proximal hub portion forming a hub assembly 138 suitable for transmitting rotational motion provided by a handpiece to inner assembly 132. Tubular portion 134 has a distal portion 140 provided with a laterally disposed cutting window 142 and a distal end spherical surface 144. Diameter 146 of distal portion 134 of inner member 132 is slightly less than the diameter of the inner lumen of distal portion 104 of outer member 102 such that that inner member 132 may be rotatably positioned therein for use. Hub assembly 138 includes hub 148, spring 150, spring retainer 152, and proximal bearing element 170 mounted to the distal end of hub 148. Distance 154 extends from the distal-most surface of hub 148 to the distal-most point on distal end spherical surface 144. When mounted in a suitable handpiece (not shown), drive tang 156 of hub 148 engages a slot in a driveshaft of the handpiece and spring retainer 152 engages a shoulder on the shaft so as to compress spring 150. Compression of spring 150 ensures that the distal surface 172 of bearing element 170 contacts proximal surface 166 of outer hub 108 so as to establish the axial position of inner assembly 132 relative to outer assembly 102.

Distal surface 172 of bearing element 170 and proximal surface 166 of outer hub 108 together form a bearing in the proximal portion of the shaver. Axial force supplied by spring 150 (or other elastic member) causes frictional heating between spacer element 170 and hub 108 when the shaver is used with at high rotational speeds. Bearing element 170 is formed from a material that will not adhere to hub 108 due to heating, the material typically being a metal, or a high temperature polymeric material such as PEEK, or a lubricious polymeric material such as PTFE.

Because the bearing of shaver 100 is proximally located between inner hub assembly 138 and outer hub assembly 106 rather than at the distal end of the inner and outer tubular members as in prior art shaver 1, precision finishing of distal end spherical surface 144 is not required, and distance 154 need not be a closely controlled dimension. These factors together significantly decrease the manufacturing costs of inner member 132. Also, the elimination of the spherical surface at the distal end of tubular member 104 (corresponding to surface 16 of tubular member 4 of prior art shaver 1)

decreases the manufacturing cost of outer assembly 102 of shaver 100 compared to assembly 2 of prior art shaver 1.

Shaver 100 operates in a manner analogous to that of prior art shaver 1. Suction supplied to the lumen of distal portion 134 of inner assembly 132, via passage 158 in inner hub 148 in communication therewith, draws tissue into contact with, and partially into, the opening formed by angular alignment of windows 114 and 142. Continued rotation of inner assembly 132 causes tissue to be cut by the cooperative action of the cutting edges of windows 114 and 142. The portion of inner cutting window 142 formed in the distal end radius does not cut soft tissue since there is cooperating edge on the outer cutting window 114, however, cutting effectiveness of the rest of cutting window 142 is not affected. The efficiency of the balance of the cutting edge is, in fact increased since tissue can be sucked into the aligned cutting windows more effectively without the restriction created by the closed distal end 12 of prior art shaver 1. The performance of shaver 100 when cutting bone will be enhanced as the removal of the closed distal end of outer tubular member 4 allows the cutting edges of inner window 142 to better access the bony surface. Resection of bone is accomplished by the inner cutting edges only and does not require cooperative interaction of the inner and outer cutting edges.

Figure 10:
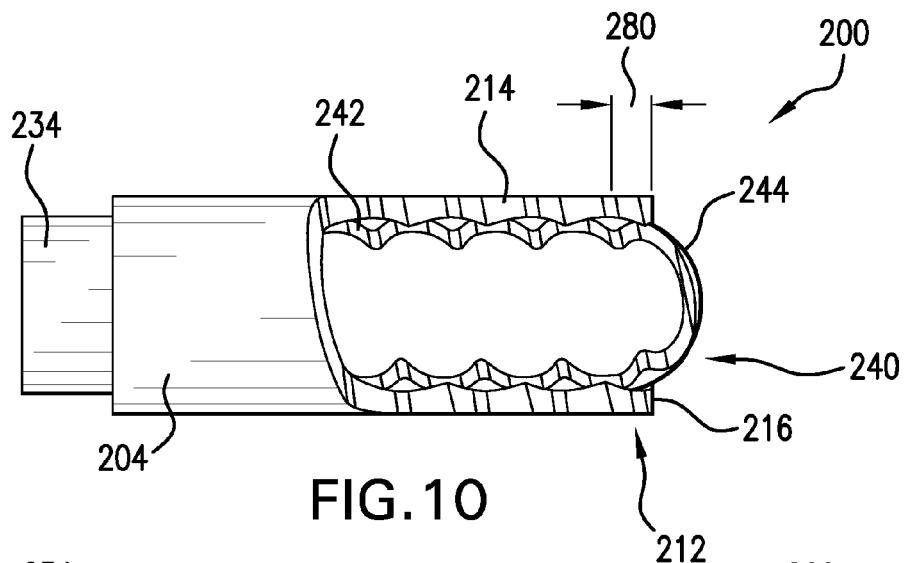
FIG. 10 is a plan view of the distal end of an alternate embodiment of the open-ended shaver assembly of FIG. 6.
Figure 11:
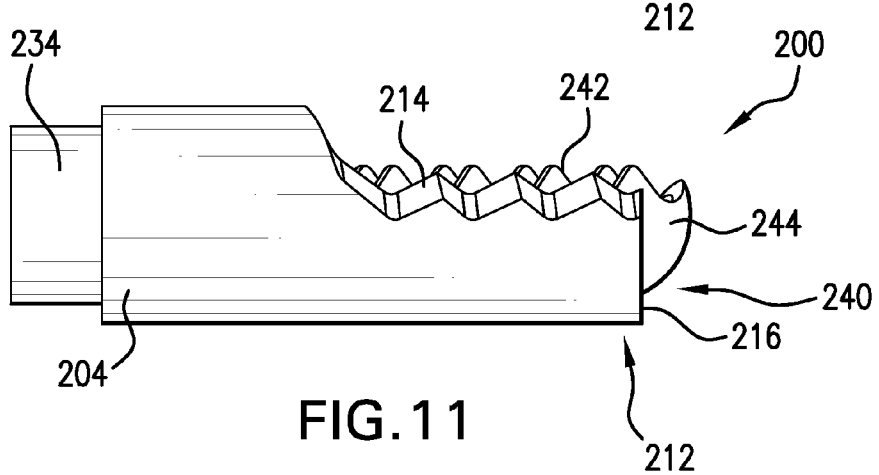
FIG. 11 is a side elevational view of the objects of FIG. 10.
Figure 12:
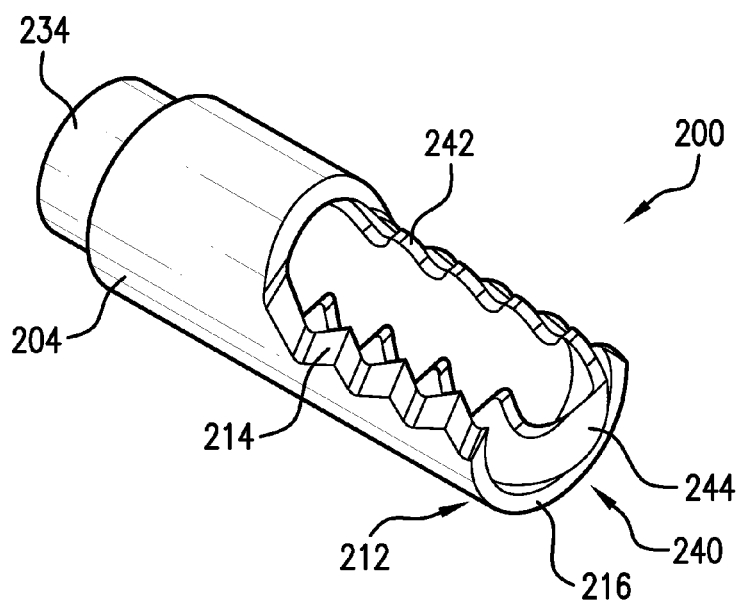
FIG. 12 is a perspective view of the objects of FIG. 10.
Figure 13:
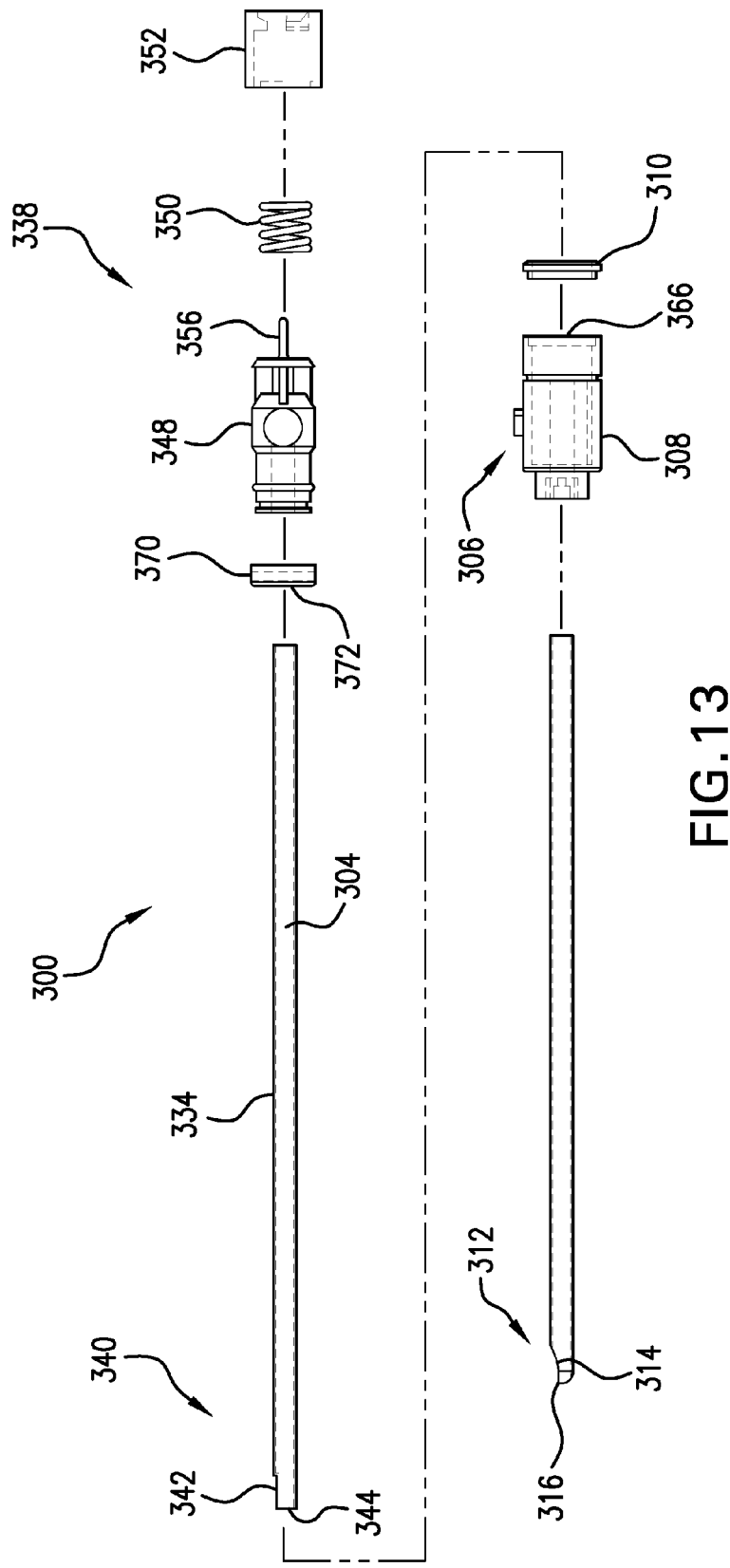
FIG. 13 is an exploded view of the inner and outer assemblies of an alternate embodiment of an open-ended shaver assembly formed in accordance with the principles of the present invention.
Figure 14:
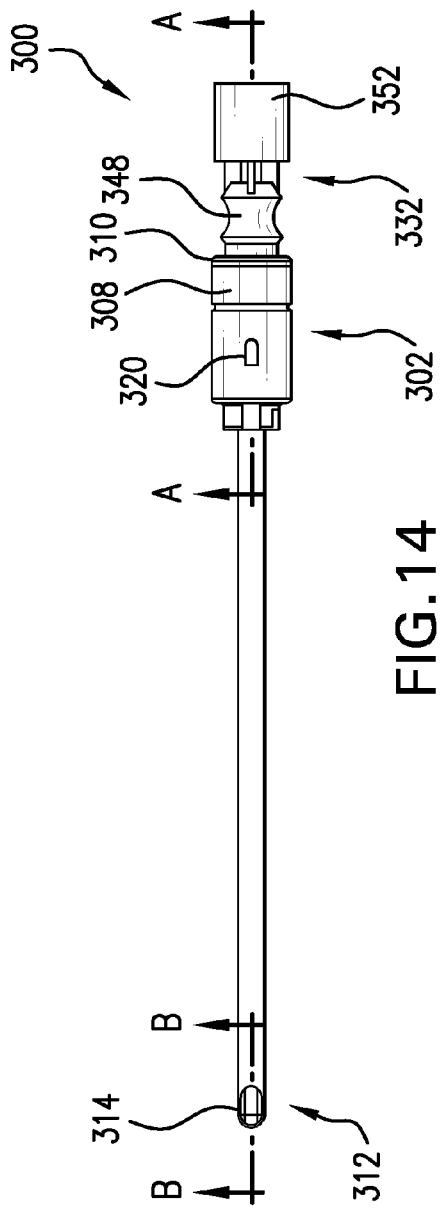
FIG. 14 is a plan view of the open-ended shaver blade assembly of FIG. 13.
Figure 16:
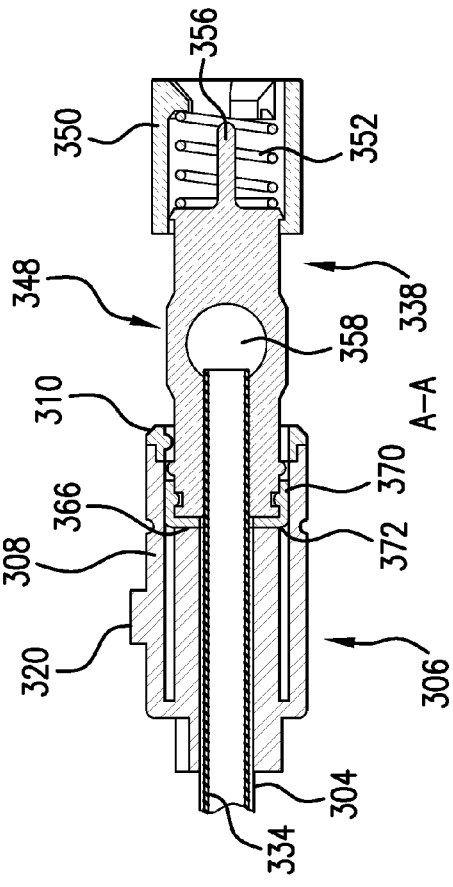
FIG. 16 is a side elevational sectional view of the proximal end of the open-ended shaver assembly of FIG. 13, at location B-B of FIG. 14.
Figure 15:
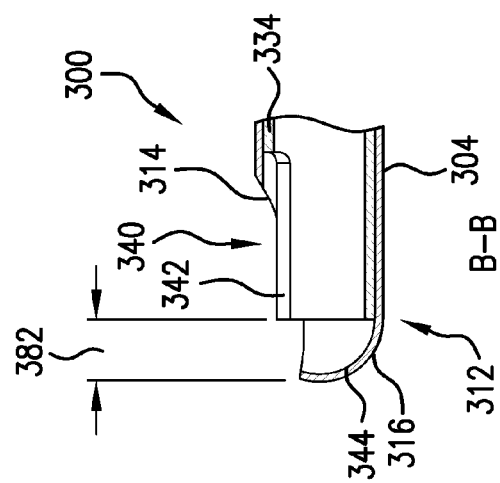
FIG. 15 is a side elevational section view of the distal end of the open-ended shaver assembly of FIG. 13, at location B-B of FIG. 14.

FIGS. 10 through 12 depict the distal portion of an alternate embodiment of open-ended shaver constructed in accordance with the principles of the present invention, shaver 200 having features for increased efficiency when cutting soft tissue. In particular, teeth have been added to the edges of cutting windows 214 and 242 to prevent tissue from being ejected from the cutting window as the edges approach. Also, distal end 216 of the outer tubular member 204 protrudes distance 280 beyond the tangency of distal radial surface 244 of inner tubular member 234. This causes a larger portion of the tissue sucked into inner window 242 to be cut by window 214 of outer member 204.

Shaver 100 and 200 described above are comprised of relatively slidable, cooperating inner and outer elongate tubular members, wherein the inner member is analogous to conventional inner member shaver bladed assemblies, being provided with a distal end spherical surface and laterally disposed cutting window proximal thereto, while the outer member is modified to have a open, typically blunt-ended distal end and a laterally disposed cutting window integral with or proximal to the open distal end. Accordingly, these embodiments of open-ended shaver are referred to as an "open ended outer" or "OEO" shavers.

An alternate embodiment of open-ended shaver is depicted in FIGS. 13 to 16. Like OEO shavers 100 and 200, shaver 300 is comprised of relatively slidable, cooperating inner and outer elongate tubular members. However, in shaver 300, it is the outer member that is analogous to conventional shaver blade assemblies, being provided with a distal end spherical surface and laterally disposed cutting window proximal thereto, while the inner member is modified to have a open, typically blunt-ended distal end and a laterally disposed cutting window integral with or proximal to the open distal end. Accordingly, the embodiment of open-ended shaver depicted in FIGS. 13 to 16 is referred to as an "open ended inner" or "OEI" shaver.

Referring now to FIGS. 13 through 16, FIG. 13 depicts an OEI shaver 300 formed in accordance with the principles of the present invention. Shaver 300 has an outer member 302, having an elongate tubular distal portion 304, typically formed from a rigid material such as metal or hard plastic, and a proximal hub portion forming a hub assembly 306 suitable for mounting in a shaver handpiece. Hub assembly 306 has a hub 308 and retainer 310. Tubular portion 304 has a distal portion 312 provided with a distal end spherical surface 116 and a laterally disposed cutting window 314. Shaver 300 also has an inner member 332, having an elongate tubular distal portion 334, typically formed from a metallic or hard polymer material, and a proximal hub portion forming a hub assembly 338 suitable for transmitting rotational motion provided by a handpiece to inner assembly 332. Tubular portion 334 has a distal portion 340 provided with a laterally disposed cutting window 342 and an open distal end surface 344. Diameter 346 of distal portion 334 of inner member 332 is slightly less than the diameter of the inner lumen of distal portion 304 of outer member 302 such that that inner member 312 may be rotatably positioned therein for use. Hub assembly 338 includes hub 348, spring 350, spring retainer 352, and proximal bearing element 370 mounted to the distal end of hub 348. Distance 354 extends from the distal-most surface of hub 348 to the distal-most point on distal end surface 344. When mounted in a suitable handpiece (not shown), drive tang 356 of hub 348 engages a slot in a driveshaft of the handpiece and spring retainer 352 engages a shoulder on the shaft so as to compress spring 350. Compression of spring 350 ensures that the distal surface 372 of bearing element 370 contacts proximal surface 366 of outer hub 308 so as to establish the axial position of inner assembly 332 relative to outer assembly 302.

Distal surface 372 of bearing element 370 and proximal surface 366 of outer hub 308 together form a bearing in the proximal portion of the shaver. Axial force supplied by spring 350 (or other elastic member) causes frictional heating between spacer element 370 and hub 308 when the shaver is used with at high rotational speeds. Bearing element 370 is formed from a material that will not adhere to hub 308 due to heating, the material typically being a metal, or a high temperature polymeric material such as PEEK, or a lubricious polymeric material such as PTFE.

Because the bearing of shaver 300 is proximally located between inner hub assembly 338 and outer hub assembly 306 rather than at the distal end of the inner and outer tubular members as in prior art shaver 1, precision finishing of distal end surface 344 is not required, and distance 354 need not be a closely controlled dimension. These factors together significantly decrease the manufacturing costs of outer member 302. Also, the elimination of the spherical surface at the distal end 340 of inner tubular member 334 (corresponding to surface 44 of tubular member 34 of prior art shaver 1) decreases the manufacturing cost of inner member 332 of shaver 300 compared to member 32 of prior art shaver 1.

Shaver 300 operates in a manner analogous to that of prior art shaver 1 as well as the previously described shavers 100 and 200 of the present invention. Suction supplied to the lumen of distal portion 334 of outer assembly 332, via passage 358 in inner hub 348 in communication therewith, draws tissue into contact with, and partially into, the opening formed by angular alignment of windows 314 and 342. Continued rotation of inner assembly 332 causes tissue to be cut by the cooperative action of the cutting edges of windows 314 and 342.

Free-Floating Shavers

As noted previously, it is a goal of the present invention to eliminate the distal bearing surface of an endoscopic cutting instrument while retaining the benefits of shavers that utilize vacuum pressure to draw tissue into the cutting window, to thereby improve cutting efficiency while at the same time reduce manufacturing costs. As discussed in greater detail below, this goal may be achieved by means of a "free-floating shaver". The free-floating shavers of the present invention are analogous to conventional endoscopic shavers with one important exception: the axial constraints characteristic of conventional shavers have been substantially reduced or eliminated. In one embodiment, this is achieved by eliminating the spring and spring retainer characteristic of conventional shaver assemblies, thereby allowing the inner member to move axially in an unrestricted fashion, within predetermined limits.

Proximal movement of the inner member may be limited by one or more coordinating features in the handpiece, the inner hub and/or in the outer hub. For example, the ability of the inner member to move laterally in the proximal direction is constrained at least in part by the fact that the outer hub assembly and the handpiece assembly are firmly locked together, typically via interaction between outer hub key element and a coordinating lock element in the handpiece assembly. This locked configuration firmly establishes the distance between the outer hub and the handpiece drive member, thereby preventing relative movement thereof. However, additional modifications may be made to further limit the ability of the inner hub member to travel.

Distal movement of the inner member may be limited by contact between the outer surface of the inner member distal end and the inner surface of the outer member distal end, the surfaces functionally as a stop rather than a bearing. I Alternatively, movement of the inner member may be controlled by means of a proximal spacer or distal limit stop positioned between the inner and outer hubs. For example, a distal limit stop or proximal spacer may be positioned between the inner and outer hubs such that contact is never made between the inner and outer distal end spherical surfaces.

When the distal limit arises from the use of a proximal spacer, it is preferable to provide for a predetermined minimum gap between the outer surface of the inner member distal end and the inner surface of the outer member distal end to prevent the formation of a distal bearing. The invention is not limited to any particular ranges of motion. However, for embodiments having one stop at the tip of the bearing surface and the other at the fork, the range of motion (i.e., the distance between the inner distal surface of the outer member and the outer distal surface of the inner member) is preferably on the order of preferably 0.005 to 0.120 inches, more preferably 0.010 to 0.080 inches. For embodiments that utilize a proximal spacer that prevents "bearing surfaces" from coming into contact, the front clearance when the inner member is at its axial distal limit should be between 0.002 to 0.100 inches, more preferably 0.002 to 0.060, even more preferably 0.005 to 0.030 inches. In other words, the total travel distance permitted for the inner member should be as above, preferably 0.005 to 0.120 inches, more preferably 0.010 to 0.080 inches.

Figure 17C:
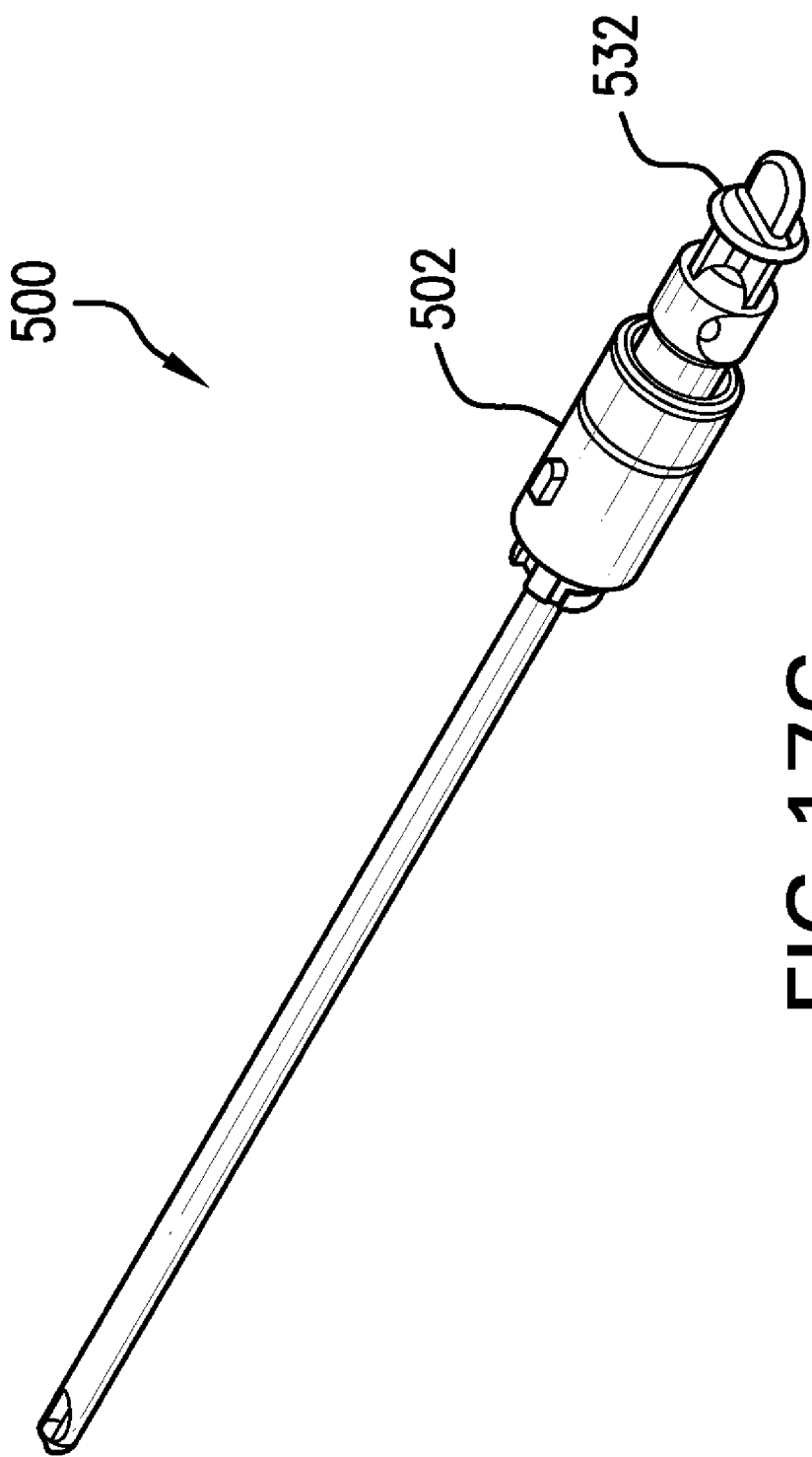
FIG. 17C is a perspective view of the free-floating shaver blade assembly of FIG. 17A.

Turning now to FIGS. 17 to 19, FIG. 17A depicts a free floating shaver 500 wherein the goals of improved cutting efficiency and reduced manufacturing costs are achieved by removing the axial constraints of the inner member that are characteristic of conventional shaver assemblies. Specifically, FIGS. 17A to 17C depict an illustrative shaver 500 formed in accordance with the principles of the present invention having an outer member 502, having an elongate tubular distal portion 504, typically formed from a rigid material such as metal or hard plastic, and a proximal hub portion forming a hub assembly 506 suitable for mounting in a shaver handpiece. Hub assembly 506 has a hub 508 and retainer 510. Tubular portion 504 has a distal portion 512 provided with a distal end spherical surface 516 and a laterally disposed cutting window 514. Shaver 500 also has an inner member 532, having an elongate tubular distal portion 534, typically formed from a metallic or hard polymer material, and a proximal hub portion forming a hub assembly 538 suitable for transmitting rotational motion provided by a handpiece to inner assembly 532. Tubular portion 534 has a distal portion 540 provided with a laterally disposed cutting window 542 and a distal end spherical surface 544. Diameter 546 of distal portion 534 of inner member 532 is slightly less than the diameter of the inner lumen of distal portion 504 of outer member 502 such that that inner member 512 may be rotatably positioned therein for use.

Shaver 500 is identical to prior art shaver 1 with the exception that spring 50 and spring retainer 52 are optionally eliminated from inner member hub assembly 538. Accordingly, hub assembly 538 simply comprises hub 548, suction passage 558 and drive tang 556. Distance 554 extends from the distal-most surface of hub 548 to the distal-most point on distal end spherical surface 544. When mounted in a suitable handpiece 2000, drive tang 556 of hub 548 engages a slot 2020 in a driveshaft of the handpiece. Because spring 50 is eliminated, inner assembly 532 travels axially freely within outer member 502 within predetermined limits of axial motion.

FIGS. 18A to 18B depict shaver 500 with inner assembly 532 at its distal-most limit of travel, outer radius 544 of inner assembly 532 being in contact with inner radius 516 of outer assembly 502. Also depicted in FIGS. 18A and 18B is drive member 2000 of a suitable handpiece in which shaver 500 is removably mounted. Slot 2020 of member 2000 engages with drive tang 556 of hub 548 so as to transmit rotational motion from member 500 to hub 548. Proximal-most surface 580 of hub 548 is displaced axially from distal-most surface 2040 of member 2000 distance 2100. Distances 2100 and 582 are equal.

Figure 19A:
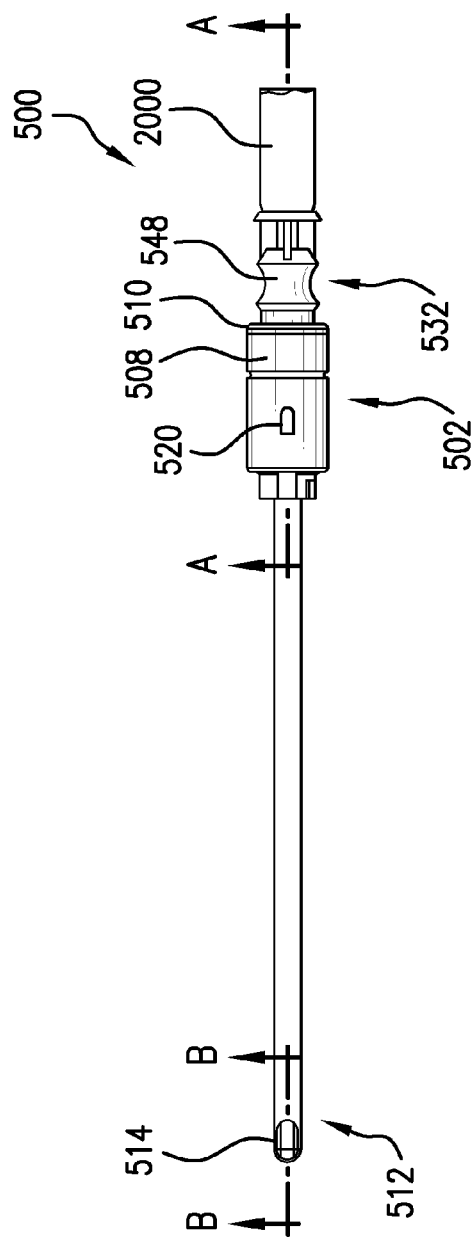
FIG. 19A is a plan view of the free-floating shaver assembly of FIG. 17, depicting the inner assembly in its most proximal position.
Figure 19C:
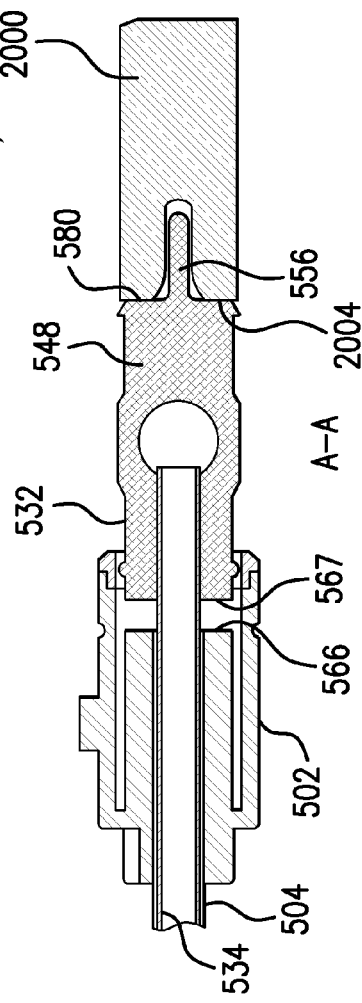
FIG. 19C is a side elevational sectional view of the proximal portion of the free-floating shaver assembly of FIG. 17, at location A-A of FIG. 18A.
Figure 19B:
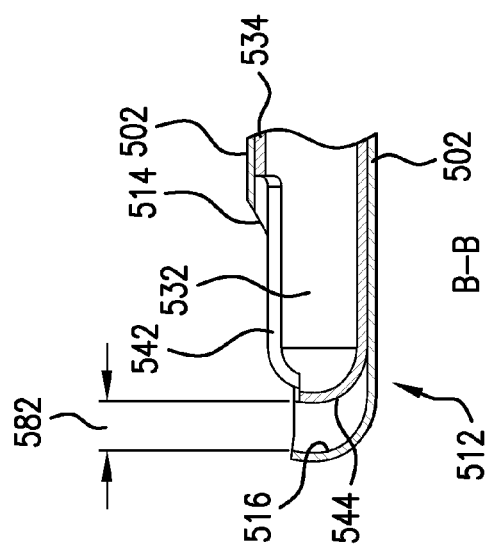
FIG. 19B is side elevational sectional view of the distal portion of the free-floating shaver assembly of FIG. 17, at location B-B of FIG. 19A.

FIGS. 19A to 19C depict shaver 500 with inner assembly 532 at its proximal-most limit of travel, proximal-most surface 580 of hub 548 being in contact with distal-most surface 2040 of member 2000. Outer radius 544 of inner assembly 532 is displaced proximally distance 582 from inner radius 516 of outer assembly 502.

Because spring 50 of prior art shaver 1 is eliminated, there is no axial loading between distal outer radius 544 of inner member 532 and distal inner radius 516 of outer member 502 such that the radii together do not form a bearing, but rather function as a stop to distally limit axial travel of inner member 532. Contact between surfaces 516 and 544 is intermittent and has a low contact force. Preload of the bearing surfaces present in prior art shaver 1 is eliminated.

Because of this, precision finishing of distal end spherical surfaces 544 and 516 is not required. This significantly decreases the manufacturing costs of assemblies 532 and 502.

Shaver 500 is used in the same manner as prior art shaver 1. Efficiency is increased because inner assembly 532 is allowed to float axially allowing the cutting edges to follow a path of least resistance when penetrating the tissue. In particular, the floating nature of the inner member allows the sharp features (e.g., teeth) of the cutting windows to better penetrate the tissue, by allowing them to incrementally yet freely the axial direction so as to follow a path of least resistance. Because the cutting features more firmly embed themselves in the tissue, less tissue is ejected from the cutting window as the inner and outer cutting edges approach each other. Because less tissue is ejected, more is resected with each window closure, thereby increasing the efficiency of the blade.

Referring now to FIGS. 20 and 21, FIG. 20A depicts a free floating shaver 600 wherein the goals of improved cutting efficiency and reduced manufacturing costs are achieved by removing the axial constraints of the inner member that are characteristic of conventional shaver assemblies while at the same time providing a means for preventing frictional contact between the corresponding distal surfaces of the inner and outer members.

Specifically, FIGS. 20A-20C depict an illustrative shaver 600 formed in accordance with the principles of the present invention having an outer member 602, having an elongate tubular distal portion 604, typically formed from a rigid material such as metal or hard plastic, and a proximal hub portion forming a hub assembly 606 suitable for mounting in a shaver handpiece. Hub assembly 606 has a hub 608 and retainer 610. Tubular portion 604 has a distal portion 612 provided with a distal end spherical surface 616 and a laterally disposed cutting window 614. Shaver 600 also has an inner member 632, having an elongate tubular distal portion 634, typically formed from a metallic or hard polymer material, and a proximal hub portion forming a hub assembly 638 suitable for transmitting rotational motion provided by a handpiece to inner assembly 632. Tubular portion 634 has a distal portion 640 provided with a laterally disposed cutting window 642 and a distal end spherical surface 644. Diameter 646 of distal portion 634 of inner member 632 is slightly less than the diameter of the inner lumen of distal portion 604 of outer member 602 such that that inner member 612 may be rotatably positioned therein for use.

Like free-floating shaver 500, free-floating shaver 600 is identical to prior art shaver 1 with the exception that spring 50 and spring retainer 52 are optionally eliminated from inner member hub assembly 638. Accordingly, hub assembly 638 simply comprises hub 648, suction passage 658 and drive tang 656. Distance 654 extends from the distal-most surface of hub 648 to the distal-most point on distal end spherical surface 644. When mounted in a suitable handpiece 2000, drive tang 656 of hub 648 engages a slot 2020 in a driveshaft of the handpiece. Because spring 50 is eliminated, inner assembly 632 travels axially freely within outer member 602 within predetermined limits of axial motion. To that end, shaver 600 is provided with a proximal spacer element 675 disposed between the inner and outer hub assemblies, the proximal spacer having a proximal surface 676 that may engage the distal surface 667 of the inner hub 648 and a distal surface 677 that may engage the proximal surface 666 of the outer hub 608, to thereby limit the axial travel of the inner member 632.

FIGS. 20B to 20C depict shaver 600 with inner assembly 632 at its proximal-most limit of travel, proximal-most surface 680 of hub 648 being in contact with distal-most surface 2040 of member 2000. Outer radius 644 of inner assembly 632 is displaced proximally distance 682 from inner radius 616 of outer assembly 602.

FIGS. 21A to 21C depict shaver 600 with inner assembly 632 at its distal-most limit of travel, outer radius 644 of inner assembly 632 being just shy of direct contact with inner radius 616 of outer assembly 602. Also depicted in FIGS. 21A and 21C is drive member 2000 of a suitable handpiece in which shaver 600 is removably mounted. Slot 2020 of member 2000 engages with drive tang 656 of hub 648 so as to transmit rotational motion from member 600 to hub 648. Proximal-most surface 680 of hub 648 is displaced axially from distal-most surface 2040 of member 2000 distance 2100.

Because spring 50 of prior art shaver 1 is eliminated, there is no axial loading between distal outer radius 644 of inner member 632 and distal inner radius 616 of outer member 602 such that the radii together do not form a bearing, but rather function as a stop to distally limit axial travel of inner member 632. Contact between surfaces 616 and 644 is intermittent and has a low contact force. Preload of the bearing surfaces present in prior art shaver 1 is eliminated. Because of this, precision finishing of distal end spherical surfaces 644 and 616 is not required. This significantly decreases the manufacturing costs of assemblies 632 and 602.

Shaver 600 is used in the same manner as prior art shaver 1. As with free-floating shaver 500, efficiency is increased with shaver 600 because inner assembly 632 is allowed to float axially allowing the cutting edges to follow a path of least resistance when penetrating the tissue. In particular, the floating nature of the inner member allows the sharp features (e.g., teeth) of the cutting windows to better penetrate the tissue, by allowing them to incrementally yet freely the axial direction so as to follow a path of least resistance. Because the cutting features more firmly embed themselves in the tissue, less tissue is ejected from the cutting window as the inner and outer cutting edges approach each other. Because less tissue is ejected, more is resected with each window closure, thereby increasing the efficiency of the blade.

Proximal Bearing Shavers

Figure 22A:
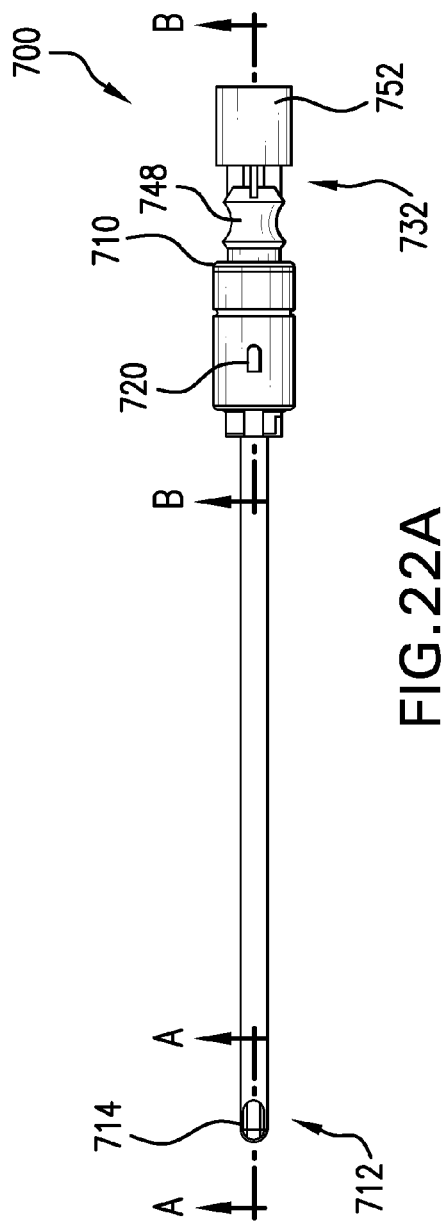
FIG. 22A is a plan view of an alternate embodiment of a shaver assembly formed in accordance with the principles of the present invention, depicting the inner assembly in its most distal position.

Referring now to FIG. 22, FIG. 22A depicts a modified shaver 700 wherein the goals of improved cutting efficiency and reduced manufacturing costs are achieved by limiting the axial constraints of the inner member that are characteristic of conventional shaver assemblies while at the same time providing a means for preventing frictional contact between the corresponding distal surfaces of the inner and outer members.

Figure 22B:
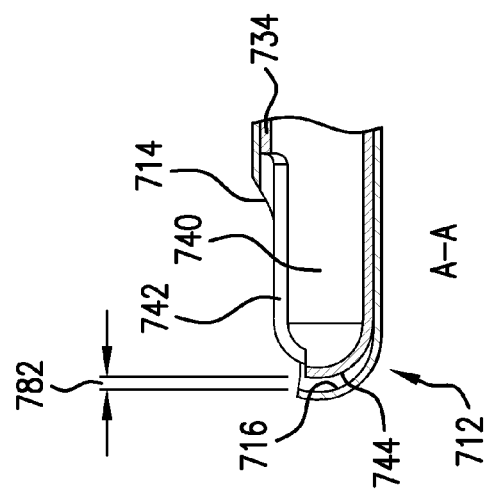
FIG. 22B is a side elevational sectional view of the distal portion of the shaver assembly of FIG. 22A, at location A-A thereof.
Figure 22C:
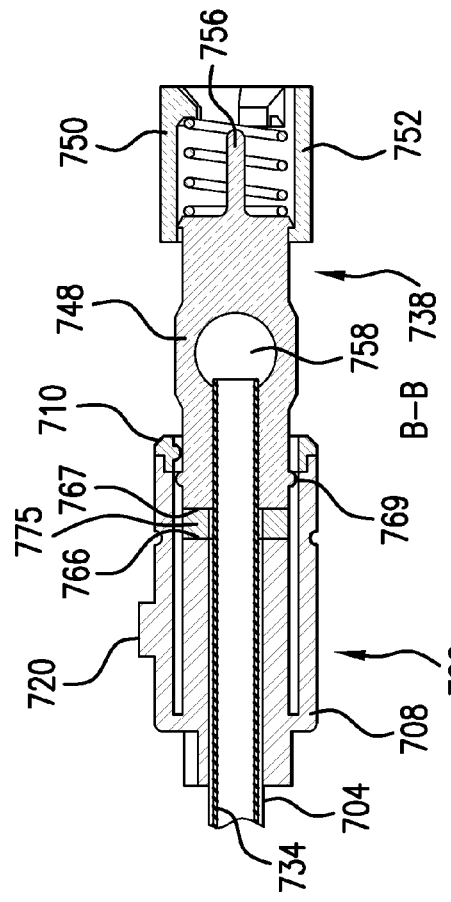
FIG. 22C is a side elevational sectional view of the proximal portion of the shaver assembly of FIG. 22A, at location B-B thereof.

Specifically, FIGS. 22A-22C depict an illustrative shaver 700 formed in accordance with the principles of the present invention having an outer member 702, having an elongate tubular distal portion 704, typically formed from a rigid material such as metal or hard plastic, and a proximal hub portion forming a hub assembly 706 suitable for mounting in a shaver handpiece. Hub assembly 706 has a hub 708 and retainer 710. Tubular portion 704 has a distal portion 712 provided with a distal end spherical surface 716 and a laterally disposed cutting window 714. Shaver 700 also has an inner member 732, having an elongate tubular distal portion 734, typically formed from a metallic or hard polymer material, and a proximal hub portion forming a hub assembly 738 suitable for transmitting rotational motion provided by a handpiece to inner assembly 732. Tubular portion 734 has a distal portion 740 provided with a laterally disposed cutting window 742 and a distal end spherical surface 744. Diameter 746 of distal portion 734 of inner member 732 is slightly less than the diameter of the inner lumen of distal portion 704 of outer member 702 such that that inner member 712 may be rotatably positioned therein for use.

Unlike free-floating shavers 500 and 600, modified shaver 700 includes the spring and spring retainer that are characteristic of prior art shaver assemblies. Accordingly, hub assembly 738 comprises hub 748, suction passage 758, drive tang 756, spring 750 and spring retainer 752. Distance 754 extends from the distal-most surface of hub 748 to the distal-most point on distal end spherical surface 744. When mounted in a suitable handpiece (not shown), drive tang 756 of hub 748 engages a slot in a driveshaft of the handpiece and spring retainer 752 engages a shoulder on the shaft so as to compress the spring. Compression of spring places pressure on inner tubular member, urging its distal toward the inner distal surface of the outer member. However, shaver 700 is provided with a proximal spacer element 775 disposed between the inner and outer hub assemblies, the proximal spacer having a proximal surface 776 that may engage the distal surface 767 of the inner hub 748 and a distal surface 777 that may engage the proximal surface 766 of the outer hub 708, to thereby limit the axial travel of the inner member 732.

FIGS. 22B to 22C depict shaver 700 with inner assembly 732 at its distal-most limit of travel, outer radius 744 of inner assembly 732 being just shy of direct contact with inner radius 716 of outer assembly 702. Because action of spring 750 of shaver 700 is restricted by means of the proximal space, there is no axial loading between distal outer radius 744 of inner member 732 and distal inner radius 716 of outer member 702 such that the radii together do not form a bearing, but rather function as a stop to distally limit axial travel of inner member 732. Contact between surfaces 716 and 744 is intermittent and has a low contact force. Preload of the bearing surfaces present in prior art shaver 1 is eliminated. Because of this, precision finishing of distal end spherical surfaces 744 and 716 is not required. This significantly decreases the manufacturing costs of assemblies 732 and 702.

Shaver 700 is used in the same manner as prior art shaver 1. As with free-floating shavers 500 and 600, efficiency is increased with shaver 700 because inner assembly 732 is allowed to float axially allowing the cutting edges to follow a path of least resistance when penetrating the tissue. In particular, the floating nature of the inner member allows the sharp features (e.g., teeth) of the cutting windows to better penetrate the tissue, by allowing them to incrementally yet freely the axial direction so as to follow a path of least resistance. Because the cutting features more firmly embed themselves in the tissue, less tissue is ejected from the cutting window as the inner and outer cutting edges approach each other. Because less tissue is ejected, more is resected with each window closure, thereby increasing the efficiency of the blade.

INDUSTRIAL APPLICABILITY

As noted previously, the present invention is directed to minimally invasive endoscopic cutting instrument having improved cutting efficiency and reduced manufacturing costs. In particular, by increasing tissue access to the cutting window and/or reducing tissue ejection, the present invention provides for improved cutting efficiency. Likewise, by eliminating or modifying the distal end axial bearing surfaces, the present invention provides for a substantial reduction in manufacturing costs.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

The invention has been illustrated by reference to specific examples and preferred embodiments. However, it should be understood that the invention is intended not to be limited by the foregoing description, but to be defined by the appended claims and their equivalents.

What is claimed:

1. An endoscopic surgical assembly comprising concentrically disposed elongated tubular inner and outer members, each of said elongated members comprising a coordinating hub disposed at its proximal end, a laterally disposed cutting aperture at its distal end, and a central lumen extending between the two ends, said inner member being sized to be slidably received within the lumen of said outer member, wherein:
   when said inner and outer hubs are connected, axial displacement between the inner and outer members is fixed and the respective cutting apertures of said inner and outer members are aligned to permit cooperative resection of tissue in contact with said apertures,
   further wherein:
   (a) the inner member comprises a, distally facing open end while the distally facing end of the outer member comprises a closed surface, or
   (b) the outer member comprises a, distally facing open end while the distally facing end of the inner member comprises a closed surface; and further comprising:
   an elastic member that transmits an axial force distally on the inner member to maintain contact between a distal surface of the inner hub and a proximal surface of the outer hub when said inner and outer hubs are connected such that the distal ends of the inner and outer members do not form a distal bearing surface.

2. The surgical assembly of claim 1, wherein said closed surface comprises a spherical surface.

3. The surgical assembly of claim 1, wherein the distally facing open end comprises a blunt surface.

4. The surgical assembly of claim 1, wherein the distally facing open end comprises an angled surface.

5. The surgical assembly of claim 1, wherein the cutting aperture of the closed-ended member is proximally spaced from the spherical distal end.

6. The surgical assembly of claim 1, wherein the cutting aperture of the open-ended member is proximally spaced from the open distal end.

7. The surgical assembly of claim 1, wherein the cutting aperture of the open-ended member is integral with the open distal end.

8. The endoscopic surgical assembly of claim 1, wherein said elastic member comprises a coiled offspring affixed to the inner hub.

9. The assembly of claim 1, wherein each of said cutting apertures has a perimeter comprised of two longitudinal cutting edges at least one transverse cutting edges.

10. The assembly of claim 9, wherein one or more of said cutting edges are beveled.

11. The assembly of claim 10, wherein one or more of said beveled cutting edges are provided with plurality of teeth.

12. The assembly of claim 11, wherein the angle of said beveled cutting edges ranges from 15 to 70 degrees.

13. An endoscopic surgical assembly comprising concentrically disposed elongated tubular inner and outer members, each of said elongated members comprising a coordinating hub disposed at its proximal end, a laterally disposed cutting aperture at its distal end, and a central lumen connecting the two, said inner member being sized to be slidably received within the lumen of said outer member, wherein:
   (a) the inner member hub includes an elastic member that transmits an axial force distally on said inner member so as to constrain proximal movement thereof;
   (b) the proximal end of the outer member hub is characterized by an outer collar concentrically disposed about an inner stem, said assembly further comprising an annular spacer element positioned between the proximal end of the inner stem and the distal end of the inner member hub so as to prevent direct contact therebetween; and
   (c) when said inner and outer hubs are connected, the respective cutting apertures of said inner and outer members are aligned to permit cooperative resection of tissue in contact with said apertures but the distal ends of the inner and outer members do not form a distal bearing surface.

14. The surgical assembly of claim 13, wherein each of said cutting apertures has a perimeter comprised of two longitudinal cutting edges at least one transverse cutting edges.

15. The assembly of claim 14, wherein one or more of said cutting edges are beveled.

16. The assembly of claim 15, wherein one or more of said beveled cutting edges are provided with plurality of teeth.

17. The assembly of claim 15, wherein the angle of said beveled cutting edges ranges from 15 to 70 degrees.

* * * * *

UNITED STATES PATENT AND TRADEMARK OFFICE
CERTIFICATE OF CORRECTION

PATENT NO. : 8,313,502 B2
APPLICATION NO. : 13/301156
DATED : November 20, 2012
INVENTOR(S) : Gary R. Heisler It is certified that error appears in the above-identified patent and that said Letters Patent is hereby corrected as shown below:

To claim 8, in column 22, line 32, after the phrase "said elastic member comprises a coiled", replace the term "offspring" with -- spring --.

Signed and Sealed this
Fifth Day of February, 2013

Teresa Stanek Rea
*Acting Director of the United States Patent and Trademark Office*